United States Patent
Minami et al.

(10) Patent No.: US 7,273,734 B2
(45) Date of Patent: Sep. 25, 2007

(54) PROCESS FOR PRODUCING A POLYESTER

(75) Inventors: Masato Minami, Kanagawa (JP);
Shinya Kozaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 312 days.

(21) Appl. No.: 11/063,776

(22) Filed: Feb. 24, 2005

(65) Prior Publication Data

US 2005/0143574 A1 Jun. 30, 2005

Related U.S. Application Data

(62) Division of application No. 10/195,712, filed on Jul. 16, 2002, now abandoned.

(30) Foreign Application Priority Data

| Jul. 16, 2001 | (JP) | ............................. 2001-215388 |
| Jul. 16, 2001 | (JP) | ............................. 2001-215392 |
| Jul. 16, 2001 | (JP) | ............................. 2001-215393 |
| Jul. 16, 2001 | (JP) | ............................. 2001-215428 |

(51) Int. Cl.
C12P 7/62 (2006.01)
C12P 7/56 (2006.01)

(52) U.S. Cl. .................. 435/135; 435/139; 435/252.7; 528/274; 536/126

(58) Field of Classification Search ................ 435/139, 435/135, 252.7; 536/126, 274
See application file for complete search history.

(56) References Cited

U.S. PATENT DOCUMENTS

| 1,838,599 A | 12/1931 | Wells et al. ................. 435/139 |
| 4,568,644 A | 2/1986 | Wang et al. ................. 435/161 |
| 4,758,345 A | 7/1988 | Francis et al. ............... 210/611 |
| 5,075,115 A | 12/1991 | Brine .......................... 424/486 |
| 5,342,641 A | 8/1994 | Masutake et al. ............ 426/549 |
| 5,371,014 A | 12/1994 | Matsuyama et al. ........ 435/280 |
| 5,415,790 A | 5/1995 | Maeda et al. ................. 252/8.6 |
| 5,453,365 A | 9/1995 | Sterzel et al. ............... 435/135 |
| 5,464,760 A | 11/1995 | Tsai et al. ................... 435/139 |
| 5,773,240 A | 6/1998 | Ozaki et al. ................... 435/41 |
| 5,798,237 A | 8/1998 | Picataggio et al. ......... 435/139 |
| 6,485,947 B1 | 11/2002 | Rajgarhia et al. ........... 435/139 |
| 6,569,989 B2 * | 5/2003 | Ohara et al. ................. 528/354 |
| 6,984,293 B2 * | 1/2006 | Cockrem et al. ............. 203/14 |

FOREIGN PATENT DOCUMENTS

| JP | 5-17503 | 1/1993 |
| JP | 5-43470 | 2/1993 |
| JP | 5-213778 | 8/1993 |
| JP | 5-244880 | 9/1993 |
| JP | 5-263367 | 10/1993 |
| JP | 5-336981 | 12/1993 |
| JP | 6-126715 | 5/1994 |
| JP | 6-157238 | 6/1994 |
| JP | 6-220213 | 8/1994 |
| JP | 7-327692 | 12/1995 |
| JP | 11-299479 | 11/1999 |
| JP | 2000-300284 | 10/2000 |
| WO | WO 94/13826 | 6/1994 |
| WO | WO 97/13842 A1 | 4/1997 |
| WO | WO 01/81610 A2 | 11/2001 |
| WO | WO 02/77252 A1 | 10/2002 |

OTHER PUBLICATIONS

Jean-Philippe Carlier et al., "Gas Chromotographic-Mass Spectra Studies After Methylation of Metabolites Produced by Some Anaerobic Bacteria in Spent Media," 493 *J. Chromatogr.* 257-273 (1989).

Nasser Khelifa et al., "Synthesis of 2-Hydroxy Acid from 2-Amino Acid by *Clostridium butyricum*," 8 *Bioorg. Med. Chem. Lett.* 3429-3434 (1998).

M. Ajioka et al., "The Basic Properties of Poly(lactic Acid) Produced by the Direct Condensation Polymerization of Lactic Acid," 3(4) *J. Environ. Polym. Degrad.* 225-234 (1995).

K. Hofvenahl et al., "Simultaneous Enzymatic Wheat Starch Saccharification and Fermentation to Lactic Acid by *Lactococcus lactis*," 52, *Appl. Microbiol. Biotechnol.* 163-169 (1999).

Shin-ichiro Abe et al., "Simultaneous Saccharification and Fermentation of Cellulose to Lactic Acid," 37 *Biotechnol Bioeng.* 93-96 (1991).

* cited by examiner

*Primary Examiner*—Herbert J. Lilling
(74) *Attorney, Agent, or Firm*—Fitzpatrick, Cella, Harper & Scinto

(57) ABSTRACT

A process for producing a polyester, the process comprising the steps of (1) fermenting a saccharide with a microorganism to obtain at least one substituted α-hydroxy acid represented by the formula: HO—CHR—COOH (wherein R represents a hydrocarbon group having 1 to 10 carbon atoms), and (2) polymerizing the substituted α-hydroxy acid or a derivative thereof.

7 Claims, No Drawings

PROCESS FOR PRODUCING A POLYESTER

This application is a division of application Ser. No. 10/195,712, filed Jul. 16, 2002, which is incorporated herein by reference.

BACKGROUND OF THE INVENTION

1. Field of the Invention

This invention relates to a process for producing a polyester, and also relates to a method of recycling hemicellulose and cellulose.

2. Related Background Art

Conventional general-purpose plastic products are polymeric compounds synthesized chiefly from petroleum resources. More specifically, polymeric compounds such as polyester, polystyrene, nylon, polyethylene, polyvinyl chloride, polyimide and polycarbonate are, in almost all cases, produced from monomers obtained using petroleum as a raw material.

The petroleum, however, is a limited resource, and is foreseen to become depleted before long. Accordingly, a technique is earnestly desired by which general-purpose plastic products are produced from new materials substitutive for the petroleum, i.e., renewable materials.

Meanwhile, the recycling of wastepaper or the like is put forward with an increase in demand for paper, which is due to the spread of personal computers and office automation machinery, the use of paper containers and so forth. However, the number of times paper can be recycled is limited, because the lengths of paper fibers decrease, and it is greatly questioned how wastepaper that is no longer recyclable or the like be disposed. On the other hand, from the viewpoint of effective utilization of resources, it is sought to utilize wastepaper or the like by means other than thermal recycling. Paper is composed primarily of cellulose. Thus, the focus of the studies is on decomposition of this cellulose so as to be reused.

Cellulose is produced in an amount of $10^9$ to $10^{11}$ tons per year, and is used in a large quantity for extensive purposes, such as structural materials, fillers, food additives and further adhesives or the like. With such use, waste cellulose also increases year by year.

Hemicellulose, which is present in vegetable tissues in a proportion of 20 to 30%, also finds its way into paper without being removed in the course of the manufacture of pulp. Its quantity can reach as much as about 20%. Thus, when the effective utilization of wastepaper is taken into account, the effective utilization of the hemicellulose component cannot be ignored. Also, hemicellulose discarded in the course of the manufacture of cellulose has been increasing along with the increase in demand for paper.

Meanwhile, starch is a polymeric compound formed by dehydrating polymerization of D-glucose, and is an important polysaccharide, inclusive of cellulose. The starch is produced from potatoes, sweet potatoes, corn and so forth. Its yield (the crop of corn) in the whole world is about four to five hundred million tons per year. It is produced in the largest quantity among natural resources, and is a renewable resource. Accordingly, starch is a promising new substitute resource for petroleum, if general-purpose plastic products can be manufactured from starch.

As techniques by which the waste cellulose is decomposed and reused, known are, e.g., a method in which hydrocarbons, such as methane and ethane, are derived from cellulose (Japanese Patent Application Laid-open No. 5-213778) and a method in which alcohols are produced from cellulose (Japanese Patent Application Laid-open No. 11-299479).

As techniques in which the waste hemicellulose is utilized, studies are made on food additives (Japanese Patent Applications Laid-open No. 5-17503 and No. 5-43470), foaming agents (Japanese Patent Application Laid-open No. 5-244880), sizing agents for fiber texturing (Japanese Patent Application Laid-open No. 5-263367), cosmetic materials (Japanese Patent Application Laid-open No. 6-157238), fiber materials (Japanese Patent Application Laid-open No. 6-220213) and so forth.

Incidentally, production of thermosetting resin materials from lignocellulose is disclosed in Japanese Patent Application Laid-open No. 6-126715, which are manufactured for use in adhesives in view of physical properties.

In order to deal with future increases in these wastes, a novel technical development is necessary to enable more efficient recycling. Accordingly, the present inventors have taken note of the fact that the increasing wastes are pulp, paper, waste starch and so forth on the one hand, and the fact that plastic materials substitutive for the petroleum are sought on the other hand, and have studied the production of plastics from saccharides. If plastics can be produced from saccharides, useful industrial produces can be provided using abundant starting materials. Also, the depletion of petroleum resources can be avoided and any environmental pollution caused by wastes can be eliminated.

SUMMARY OF THE INVENTION

Accordingly, an object of the present invention is to provide a practical process by which saccharides can be converted into plastics.

Stated specifically, an object of the present invention is to provide a process for producing a plastic material obtained using hemicellulose and cellulose as raw materials.

Another object of the present invention is to provide a method of recycling hemicellulose and cellulose.

Still another object of the present invention is to obtain high-quality plastics using glucans, such as cellulose and starch, as starting materials.

The present invention is a process for producing a polyester, the process comprising the steps of:

(1) fermenting a saccharide with a microorganism to obtain at least one substituted α-hydroxy acid represented by the formula: HO—CHR—COOH (wherein R represents a hydrocarbon group having 1 to 10 carbon atoms); and (2) polymerizing the substituted α-hydroxy acid or a derivative thereof.

As the saccharide, starch, glucose or xylose may be used.

In the case when the saccharide is glucose or xylose, the process may preferably have, prior to the steps (1) and (2), the step of (3) subjecting a raw material containing cellulose or hemicellulose, to hydrolysis to obtain glucose or xylose.

In the case when the saccharide is starch or glucose, the above at least one substituted α-hydroxy acid is selected from the group consisting of lactic acid (the R is a methyl group), β-phenyllactic acid (the R is a benzyl group) and 2-hydroxyisocaproic acid (the R is an isobutyl group).

The microorganism used in the step (1) may preferably be an anaerobic bacterium, and the fermentation in that step may preferably be carried out in the presence of pyruvic acid.

The substituted α-hydroxy acid may preferably be a cyclic dimer lactide, and the process may preferably have, prior to the step-(2) polymerization, the step of (4) dehydrating the substituted α-hydroxy acid by two molecules to effect cyclic diesterification to obtain the cyclic dimer lactide.

The polyester may further contain at lest one of repeating units represented by the following Formulas (I) to (III).

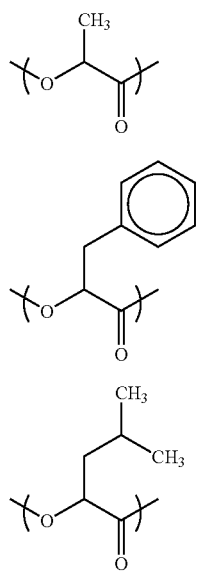

The present invention is also a process for producing a substituted α-hydroxy acid, comprising fermenting a saccharide with a microorganism.

The microorganism may preferably be an anaerobic bacterium, and the fermentation may be carried out in the presence of pyruvic acid.

DETAILED DESCRIPTION OF THE PREFERRED EMBODIMENTS

The present invention is a process for producing a polyester, which has the steps of:

(1) fermenting a saccharide with a microorganism to obtain at least one substituted α-hydroxy acid represented by the formula: HO—CHR—COOH (wherein R represents a hydrocarbon group having 1 to 10 carbon atoms); and (2) polymerizing the substituted α-hydroxy acid or a derivative thereof.

The step (1) may specifically include the following four embodiments.

A first embodiment is a polyester production process, which comprises hydrolyzing a glucan to obtain glucose, fermenting the glucose with a microorganism to produce the substituted α-hydroxy acid, and polymerizing the substituted α-hydroxy acid or a substituted α-hydroxy acid derivative.

A second embodiment is a polyester production process, which comprises fermenting starch with a microorganism to produce the substituted α-hydroxy acid, and polymerizing the substituted α-hydroxy acid or a substituted α-hydroxy acid derivative.

A third embodiment is a polyester production process, which comprises hydrolyzing a material containing at least hemicellulose, to obtain xylose, fermenting the xylose with a microorganism to produce the substituted α-hydroxy acid, and polymerizing the substituted α-hydroxy acid or a substituted hydroxy acid derivative.

A fourth embodiment is a polyester production process, which comprises hydrolyzing a material containing hemicellulose and cellulose, to obtain xylose and glucose, fermenting the xylose and glucose with a microorganism to produce the substituted α-hydroxy acid, and polymerizing the substituted α-hydroxy acid or a substituted α-hydroxy acid derivative.

As the microorganism used in the above first to fourth embodiments, an anaerobic bacterium is preferred. The anaerobic bacterium may preferably be a bacterium of the genus *Clostridium*. The bacterium of the genus *Clostridium* may preferably be *Clostridium beijerinckii* strain HICA432, FERMP-18373, capable of forming the substituted α-hydroxy acid from glucose.

In the production process of the present invention, substituted α-hydroxy acids having a purity high enough to be usable as a polyester monomer can efficiently be produced from a saccharide, such as starch, glucose, xylose or a mixture of glucose and xylose, by utilizing a microorganism. As a result, a high-quality plastic can be obtained using glucans, such as cellulose and starch, cellulose, hemicellulose and a mixture of glucose and xylose as starting materials. Hence, a polyester can be produced, which is obtained using waste cellulose, waste hemicellulose, waste starch and so forth as raw materials. Thus, these wastes can be recycled.

A. The step of obtaining substituted α-hydroxy acid:

First Embodiment

The process of the first embodiment comprises the step of hydrolyzing a glucan to obtain glucose, and the step of fermenting the glucose with a microorganism to obtain at least one substituted α-hydroxy acid represented by the formula: HO—CHR—COOH (wherein R represents a hydrocarbon group having 1 to 10 carbon atoms).

The respective steps are described below.

Glucose from Glucan

As the glucan serving as a starting material, there are no particular limitations thereon as long as it can be hydrolyzed to form glucose. However, from the viewpoint of the recycling of glucan, cellulose and starch are preferred, which are produced in large quantities and have not been usefully recycled.

The conversion of cellulose into glucose may be made by, e.g., a method of decomposing the cellulose with an enzyme, such as cellulase, a method of decomposing it with an acid, such as sulfuric acid or hydrochloric acid, or a method of decomposing it with supercritical water.

As the cellulose used as a raw material when the glucose is obtained from cellulose, any commercially available cellulose may be used as a matter of course, and any waste cellulose obtained by treating waste paper and woods, such as waste wood, may also be used as appropriate under the circumstances. Thus, the present invention can present a new route for the recycling of waste cellulose.

The conversion of starch into glucose may be made by, e.g., a method of hydrolyzing the starch with a dilute acid, such as dilute sulfuric acid, a method of hydrolyzing it with an enzyme, such as amylase or maltase, or a method of hydrolyzing it with supercritical water.

As the starch used as a raw material when the glucose is obtained from starch, any commercially available starch may be used as a matter of course, and any waste starch, obtained by treating potatoes, sweet potatoes and corn may also be used, as appropriate under the circumstances. Thus, the present invention can make a new route for the recycling of waste starch.

Substituted α-Hydroxy Acid from Glucose

The conversion of glucose into substituted α-hydroxy acids is carried out by anaerobic fermentation attributable to a microorganism. Incidentally, the production of hydroxy acids by microorganisms is disclosed in Japanese Patent Applications Laid-open No. 5-336981 and No. 7-327692. There is, however, no specific disclosure as to any microorganisms capable of producing 2-hydroxyisocaproic acid from glucose.

There are only few microorganisms isolated and identified as strains capable of producing a substituted α-hydroxy acid from glucose, and these compounds can only be produced at a low efficiency. Accordingly, we have extensively screened new strains. For example, the 2-hydroxyisocaproic acid has been picked up as the substituted α-hydroxy acid, and, using a VL culture medium (10 g/l of peptone, 5 g/l of yeast extract, 2 g/l of meat extract, 5 g/l of NaCl and 2 g/l of cysteine hydrochloride) to which 5 g/l of glucose and 5 g/l of calcium carbonate have been added, and under anaerobic conditions of 30° C., screening has been made on strains having the ability to produce the 2-hydroxyisocaproic acid.

As a result, we have succeeded in obtaining a *Clostridium beijerinckii* strain HICA432 as a strain capable of producing 2-hydroxyisocaproic acid from glucose, which is a bacterium of the genus *Clostridium*, such as *Clostridium beijerinckii*.

The above strain is kept deposited as of Jun. 6, 2001 in International Patent Organism Depositary (IPOD), National Institute of Advanced Industrial Science and Technology (AIST) (Deposition No. FERMP-18373). This deposit was transferred on Jul. 15, 2002 with deposit number FERM BP-8117 to an international deposit under the terms of the Budapest Treaty on the International Recognition of the Deposit of Microorganisms for the Purposes of Patent Procedure in the International Patent Organism Depositary (IPOD), National Institute of Advanced Industrial Science and Technology (AIST) at AIST Tsukuba Central 6, 1-1, Higashi 1-chome Tsukuba-shi, Ibaraki-ken 305-8566, Japan.

On the *Clostridium beijerinckii* strain HICA432, FERMP-18373, thus obtained, products formed from glucose have further been analyzed to find that, in addition to the 2-hydroxyisocaproic acid as the substituted α-hydroxy acid represented by HO—CHR—COOH (R is an isobutyl group), at least lactic acid (R is a methyl group) and β-phenyllactic acid (R is a benzyl group) have been produced. Hence, polyester can be produced from at least one of these substituted α-hydroxy acids.

Stated specifically, when the substituted α-hydroxy acids produced from glucose by the aid of the strain HICA432 are used, the polyester obtained has at lest one of the repeating units represented by the above Formulas (I) to (III).

A mixture of the substituted α-hydroxy acids produced from glucose by the aid of the strain HICA432 may further optionally be purified to obtain, e.g., one containing substantially only β-phenyllactic acid, one containing substantially only 2-hydroxyisocaproic acid, one containing at least β-phenyllactic acid, and one containing at least 2-hydroxyisocaproic acid.

Where at least one substituted α-hydroxy acid is so purified as to contain substantially only the β-phenyllactic acid, the polyester obtained chiefly contains the structure represented by Formula (II). In this case, the polyester obtained has a benzyl group in the side chain, and hence is presumed to have superior heat resistance. Also, the β-phenyllactic acid has a high polymerization activity, and hence can ensure a sufficient degree of polymerization of the polyester obtained.

What is meant by "chiefly contain" is that the product preferably comprise 60 mol % or more, more preferably 70 mol % or more, still more preferably 80 mol % or more, and most preferably 90 mol % or more.

Where at least one substituted α-hydroxy acid is so purified as to contain substantially only the 2-hydroxyisocaproic acid, the polyester obtained chiefly contains the structure represented by Formula (III). In this case, the polyester obtained has an isobutyl group in the side chain, and hence is presumed to have a low glass transition temperature and superior mechanical properties. Also, the 2-hydroxyisocaproic acid has a high polymerization activity, and hence can ensure a sufficient degree of polymerization of the polyester obtained.

Where at least one substituted α-hydroxy acid is so purified as to contain at least the β-phenyllactic acid and where, e.g., it is so purified as to contain lactic acid and β-phenyllactic acid, a polyester can be produced, which chiefly contains the structures represented by Formulas (I) and (II). In this case, the polyester obtained has a methyl group and a benzyl group in the side chain, and hence is presumed to have well-balanced moldability and heat resistance.

Where at least one substituted α-hydroxy acid is so purified as to contain at least the 2-hydroxyisocaproic acid and where, e.g., it is so purified as to contain lactic acid and 2-hydroxyisocaproic acid, a polyester can be produced, which chiefly contains the structures represented by Formulas (I) and (III). In this case, the polyester obtained has a methyl group and an isobutyl group in the side chain, and hence is presumed to have well-balanced moldability and mechanical properties.

Where at least one substituted α-hydroxy acid is so purified as to contain at least the β-phenyllactic acid and the 2-hydroxyisocaproic acid, a polyester can be produced, which chiefly contains the structures represented by Formulas (II) and (III). In this case, the polyester obtained has a benzyl group and an isobutyl group in the side chain, and hence is presumed to have well-balanced heat resistance and mechanical properties. Also, the β-phenyllactic acid and 2-hydroxyisocaproic acid have a high polymerization activity, and hence can ensure a sufficient degree of polymerization of the polyester obtained.

The substituted α-hydroxy acids may also individually be purified, and the purified products obtained may be mixed in stated quantities to produce a polyester. In this case, a wide range of physical properties of the polyester can be materialized.

The *Clostridium beijerinckii* strain HICA432, FERMP-18373, can produce the substituted α-hydroxy acid at a high rate. Stated specifically, when compared under the same growth conditions, the strain HICA432 can achieve in a few days the quantity of the substituted α-hydroxy acid, which any conventional, commonly known absolutely anaerobic bacteria and having the ability to produce substituted α-hydroxy acids is only able to produce in a few weeks to a few months. Hence, a sufficient production efficiency of the substituted α-hydroxy acid can be materialized.

The *Clostridium beijerinckii* strain HICA432, FERMP-18373, also has a high growth rate. Stated specifically, while any of commonly available absolutely anaerobic bacteria reach the initial logarithmic growth phase about a month after inoculation, the strain HICA432 reaches the initial logarithmic growth phase in a few days. Hence, the quantity of the bacterial body necessary for producing the substituted α-hydroxy acid in a sufficient quantity can be ensured with ease.

The fermentation for converting the glucose into the substituted α-hydroxy acid is carried out by adding the strain to a culture fluid containing the glucose as a chief carbon source and also containing nitrogen, phosphorus, mineral(s), vitamin(s) and so forth added thereto as nutrients, and maintaining it under anaerobic conditions.

The above strain is an absolutely anaerobic bacterium, which dies out in the presence of oxygen, and hence the anaerobic conditions must be strictly set up. After the culture medium has been injected, the gaseous-phase portion in a culturing container, hermetically closed with a butyl rubber stopper or the like not transmitting any gases, is displaced with nitrogen, carbon dioxide, hydrogen or the like. Any oxygen in the culture medium must also be removed using a reducing agent, such as cysteine, sodium thioglycolate or sodium sulfide, or by heat treatment or exposure to nitrogen.

The concentration of glucose in the culture fluid may be set in accordance with the type of the microorganism used. In order to materialize the production of a sufficient quantity of substituted α-hydroxy acids, the glucose may usually be in a concentration of 0.1% by weight or more, and preferably 0.5% by weight or more. On the other hand, in order to produce fewer by-products, it may usually be in a concentration of 10% by weight or less, and preferably 5% by weight or less.

Any auxiliary carbon sources are unnecessary, and the glucose may be used as a single carbon source. As nitrogen sources, usable are organic or inorganic nitrogen sources, such as urea, ammonia, ammonium sulfate and ammonium nitrate, and natural nitrogen sources, such as corn steep liquor, peptone, meat extract and yeast extract. As inorganic salts, usable are potassium phosphate, sodium phosphate, magnesium sulfate, manganese sulfate, ferrous sulfate, potassium chloride and sodium chloride.

Fermentation temperature may usually be set at 15° C. or above, and preferably 20° C. or above, in order to produce a sufficient quantity of substituted α-hydroxy acids. On the other hand, in order to produce fewer by-products and prevent the strain from dying out, it may usually be set at 38° C. or less, and preferably 37° C. or less.

The culture fluid may also usually have a pH of approximately from 5 to 7 at a suitable temperature, which may appropriately be set in accordance with the nature of the microorganism.

Further with regard to fermentation time, which depends on the type of the microorganism, in the case of the strain HICA432, the fermentation can be completed in three days to a week, or, under selected conditions for pre-fermentation, in one to three days.

A phenomenon has also been found in which, with progress of fermentation, the strain HICA432 changes the proportion of the substituted α-hydroxy acids it produces. For example, where the fermentation is performed under the conditions described above, the lactic acid, β-phenyllactic acid and 2-hydroxyisocaproic acid are produced in substantially the same molar number in the former term of the fermentation (e.g., up to the third day after the start of fermentation), and their molar concentrations in the culture medium increase in a similar manner. In contrast, in the latter term of the fermentation (e.g., on the third day and later after the start of fermentation), the molar concentration of the lactic acid, β-phenyllactic acid and 2-hydroxyisocaproic acid in the culture medium becomes constant and only that of lactic acid increases.

Such performance may be utilized so that the substituted α-hydroxy acids can be more efficiently purified. For example, where the β-phenyllactic acid and 2-hydroxyisocaproic acid are chiefly needed, a mixture of substituted α-hydroxy acids produced in the former term of the fermentation is purified. On the other hand, where the lactic acid is chiefly needed, a mixture of substituted α-hydroxy acids produced in the latter term of the fermentation is purified.

It has further been found that such fermentation performance can be controlled by adding pyruvic acid to the culture medium. For example, where the fermentation is performed adding pyruvic acid to the culture medium, lactic acid, β-phenyllactic acid and 2-hydroxyisocaproic acid are produced in substantially the same molar number in the former term of the fermentation (e.g., up to the third day after the start of fermentation), and their molar concentrations in the culture medium increase in a similar manner. In contrast, in the latter term of the fermentation (e.g., on the third day and later after the start of fermentation), the molar concentration of the 2-hydroxyisocaproic acid in the culture medium becomes constant, whereas the molar concentration of the lactic acid decreases and that of the β-phenyllactic acid increases.

Such performance may be utilized so that the substituted α-hydroxy acids can be more efficiently purified. For example, where the β-phenyllactic acid and 2-hydroxyisocaproic acid are chiefly needed, a mixture of substituted α-hydroxy acids produced in the former term of the fermentation is purified. On the other hand, where only the β-phenyllactic acid is chiefly needed, a mixture of substituted α-hydroxy acids produced in the latter term of the fermentation is purified.

Here, the pyruvic acid may preferably be in a concentration of 0.1% by weight or more, and more preferably 0.5% by weight or more, in order to control well the formation of lactic acid. On the other hand, in order to reduce the development of by-products, it may preferably be in a concentration of 10% by weight or less, and more preferably 5% by weight or less.

Second Embodiment

The process of the second embodiment comprises the step of fermenting starch with a microorganism to obtain at least one substituted α-hydroxy acid represented by the formula: HO—CHR—COOH (wherein R represents a hydrocarbon group having 1 to 10 carbon atoms).

This step is described below.

Substituted α-Hydroxy Acid from Starch

As the starch as a raw material, any commercially available starch may be used as a matter of course, and any waste starch obtained by treating potatoes, sweet potatoes and corn may also be used, as appropriate under the circumstances. Thus, the present invention can provide a new route for the recycling of waste starch.

The step of obtaining substituted α-hydroxy acids directly from starch without passing through glucose is carried out by anaerobic fermentation attributable to a microorganism.

Incidentally, the production of hydroxy acids by microorganisms is disclosed in Japanese Patent Applications Laid-open No. 5-336981, No. 7-327692 and No. 2000-300284. There is, however, no specific disclosure as to any microorganisms capable of producing substituted α-hydroxy acids from starch.

There are only few microorganisms isolated and identified as strains capable of producing the substituted α-hydroxy acid from glucose. These compounds can only be produced by such microorganisms at a low efficiency. Accordingly, we have extensively screened new strains. Here, for the reasons of experiment efficiency and so forth, not the direct screening of strains capable of converting the starch into the substituted α-hydroxy acid was used, but screening was first conducted for strains capable of converting glucose into the substituted α-hydroxy acid, and then, from among the strains obtained, further screening was conducted for strains capable of converting the starch into the substituted α-hydroxy acid.

For example, the 2-hydroxyisocaproic acid has been picked up as the substituted α-hydroxy acid, and, using a VL culture medium (10 g/l of peptone, 5 g/l of yeast extract, 2 g/l of meat extract, 5 g/l of NaCl and 2 g/l of cysteine hydrochloride) to which 5 g/l of glucose and 5 g/l of calcium carbonate have been added, and under anaerobic conditions of 30° C., screening was conducted for strains having the ability to produce the 2-hydroxyisocaproic acid.

Then, for the strains thus obtained, the ability to produce substituted α-hydroxy acids from starch was studied.

As a result, we have succeeded in obtaining the *Clostridium beijerinckii* strain HICA432 as a strain capable of producing 2-hydroxyisocaproic acid from starch, which is a bacterium of the genus *Clostridium*, such as *Clostridium beijerinckii*.

On the *Clostridium beijerinckii* strain HICA432, FERMP-18373, thus obtained, products formed from starch have further been analyzed to find that, like the products formed from the glucose described in the first embodiment, in addition to the 2-hydroxyisocaproic acid as the substituted α-hydroxy acid represented by HO—CHR—COOH (R is an isobutyl group), at least lactic acid (R is a methyl group) and β-phenyllactic acid (R is a benzyl group) have been produced. Hence, polyester can be produced from at least one of these substituted α-hydroxy acids.

Stated specifically, also when the substituted α-hydroxy acids produced from starch by the aid of the strain HICA432 are used, the polyester obtained has at lest one of the repeating units represented by the above Formulas (I) to (III).

A mixture of the substituted α-hydroxy acids produced from starch by the aid of the strain HICA432 may optionally be purified in the same manner as in the first embodiment.

The growth rate of the strain HICA432 and the production rate of the substituted α-hydroxy acids have also been found to be the same as those of the strain used in the first embodiment.

The fermentation for converting the starch into the substituted α-hydroxy acid is carried out by adding the strain to a culture fluid containing the starch as a chief carbon source and also nitrogen, phosphorus, mineral(s), vitamin(s) and so forth added thereto as nutrients, and maintaining it under anaerobic conditions.

The above strain is an absolutely anaerobic bacterium, which dies out in the presence of oxygen, and hence the anaerobic conditions must be strictly set up. After the culture medium has been injected, the gaseous-phase portion in a culturing container, hermetically closed with a butyl rubber stopper or the like not transmitting any gases, is displaced with nitrogen, carbon dioxide, hydrogen or the like. Any oxygen in the culture medium must also be removed using a reducing agent, such as cysteine, sodium thioglycolate or sodium sulfide or by heat treatment or exposure to nitrogen.

The concentration of starch in the culture fluid may be set in accordance with the type of the microorganism used. In order to materialize the production of a sufficient quantity of substituted α-hydroxy acids, the starch may usually be in a concentration of 0.1% by weight or more, and preferably 0.5% by weight or more. On the other hand, in order to produce fewer by-products, it may usually be in a concentration of 10% by weight or less, and preferably 5% by weight or less.

Any auxiliary carbon sources are unnecessary, and the starch may be used as a single carbon source. As nitrogen sources, usable are organic or inorganic nitrogen sources, such as urea, ammonia, ammonium sulfate and ammonium nitrate, and natural nitrogen sources, such as corn steep liquor, peptone, meat extract and yeast extract. As inorganic salts, usable are potassium phosphate, sodium phosphate, magnesium sulfate, manganese sulfate, ferrous sulfate, potassium chloride and sodium chloride.

Fermentation temperature may usually be set at 15° C. or above, and preferably 20° C. or above, in order to materialize the production of a sufficient quantity of substituted α-hydroxy acids. On the other hand, in order to produce fewer by-products and prevent the strain from dying out, it may usually be set at 38° C. or below, and preferably 37° C. or below.

The culture fluid may also usually have a pH of approximately from 5 to 7 at a suitable temperature, which may appropriately be set in accordance with the nature of the microorganism.

Further with regard to fermentation time, which depends on the type of the microorganism, in the case of the strain HICA432, the fermentation can be completed in three days to a week, or, under selected conditions for pre-fermentation, in one to three days.

A phenomenon has also been found in which, with the progress of fermentation, the strain HICA432 changes the proportion of the substituted α-hydroxy acids it produces. For example, where the fermentation is performed under the conditions described above, the lactic acid, β-phenyllactic acid and 2-hydroxyisocaproic acid are produced in substantially the same molar number in the former term of the fermentation (e.g., up to the third day after the start of fermentation), and their molar concentrations in the culture medium increase in a similar manner. In contrast, in the latter term of the fermentation (e.g., on the third day and later after the start of fermentation), that of the lactic acid decreases.

Such performance may be utilized so that the substituted α-hydroxy acids can be more efficiently purified. For example, where the β-phenyllactic acid and 2-hydroxyisocaproic acid are chiefly needed, a mixture of substituted α-hydroxy acids produced in the former term of the fermentation is purified.

Third Embodiment

The process of the third embodiment comprises the step of hydrolyzing a material containing at least hemicellulose, to obtain xylose, and the step of fermenting the xylose with a microorganism to obtain at least one substituted α-hydroxy acid represented by the formula: HO—CHR—COOH (wherein R represents a hydrocarbon group having 1 to 10 carbon atoms).

These steps are described below.

Xylose from Hemicellulose

As materials containing the raw material hemicellulose, any commercially available hemicellulose may be used as a matter of course, and any waste hemicellulose obtained by appropriately treating waste paper, woods, such as waste wood, as well as pulp waste liquor may also be used. Thus, the establishment of a method of synthesizing polyester from hemicellulose can provide a new route for the recycling waste hemicellulose. In this regard, the polyester production process of the present invention is at the same time a useful method of recycling hemicellulose.

The conversion of hemicellulose into xylose may be made by, e.g., a method of decomposing the hemicellulose with an enzyme, such as xylanase, a method of decomposing it with an acid, such as sulfuric acid or hydrochloric acid, or a method of decomposing it with supercritical water.

Substituted α-Hydroxy Acid from Xylose

The conversion of xylose into substituted α-hydroxy acids is carried out by anaerobic fermentation attributable to a microorganism. Incidentally, the production of hydroxy acids by microorganisms is disclosed in Japanese Patent Applications Laid-open No. 5-336981, No. 7-327692 and No. 2000-300284. There is, however, no specific disclosure as to any microorganisms capable of producing substituted α-hydroxy acids from xylose.

There are only a few microorganisms isolated and identified as strains capable of producing the substituted α-hydroxy acid from glucose, and these compounds can only be produced at a low efficiency. Accordingly, we have extensively screened for new strains. Here, for the reasons of experiment efficiency and so forth, not the direct screening of strains capable of converting the xylose into the substituted α-hydroxy acid was conducted, but, like that made in the first embodiment, screening was first conducted for strains capable of converting glucose into the substituted α-hydroxy acid, and then, from among the strains obtained, further screening was conducted for strains capable of converting the xylose into the substituted α-hydroxy acid.

For example, the 2-hydroxyisocaproic acid has been picked up as the substituted α-hydroxy acid, and, using a VL culture medium (10 g/l of peptone, 5 g/l of yeast extract, 2 g/l of meat extract, 5 g/l of NaCl and 2 g/l of cysteine hydrochloride) to which 5 g/l of glucose and 5 g/l of calcium carbonate have been added, and under anaerobic conditions of 30° C., screening was conducted for strains having the ability to produce the 2-hydroxyisocaproic acid.

Then, on the strains thus obtained, the ability to produce substituted α-hydroxy acids from xylose was studied.

As a result, we have succeeded in obtaining the *Clostridium beijerinckii* strain HICA432 as a strain capable of producing 2-hydroxyisocaproic acid from xylose, which is a bacterium of the genus *Clostridium*, such as *Clostridium beijerinckii*.

On the *Clostridium beijerinckii* strain HICA432, FERMP-18373, thus obtained, products formed from xylose have further been analyzed to find that, in addition to the 2-hydroxyisocaproic acid as the substituted α-hydroxy acid represented by HO—CHR—COOH (R is an isobutyl group), at least β-phenyllactic acid (R is a benzyl group) has been produced. Hence, a polyester can be produced from at least one of these substituted α-hydroxy acids.

Thus, when the xylose is used as a single carbon source, as being different from the case in which the glucose or starch is used as the carbon source as described in the first and second embodiments, the strain HICA432 does not substantially produce any lactic acid.

Hence, when the substituted α-hydroxy acids produced from xylose by the aid of the strain HICA432 are used, the polyester obtained has at lest one of the repeating units represented by the above Formulas (II) and (III).

A mixture of the 2-hydroxyisocaproic acid and β-phenyllactic acid produced from xylose may optionally be purified to obtain a product containing substantially only the β-phenyllactic acid and a product containing substantially only the 2-hydroxyisocaproic acid. The structures, physical properties and so forth of the purified products thus obtained are the same as those of the purified products obtained from glucose as described in the first embodiment.

The 2-hydroxyisocaproic acid and β-phenyllactic acid may also individually be purified, and the purified products obtained may be mixed in stated quantities to produce a polyester. In this case, a wide range of physical properties of the polyester can be materialized.

The fermentation for converting the xylose into the substituted α-hydroxy acid is carried out by adding the strain to a culture fluid containing the xylose as a chief carbon source, and also containing nitrogen, phosphorus, mineral(s), vitamin(s) and so forth, added thereto as nutrients, and maintaining it under anaerobic conditions.

The above strain is an absolutely anaerobic bacterium, which dies out in the presence of oxygen, and hence the anaerobic conditions must be strictly set up. After the culture medium has been injected, the gaseous-phase portion in a culturing container hermetically closed with a butyl rubber stopper or the like not transmitting any gases is displaced with nitrogen, carbon dioxide, hydrogen or the like. Any oxygen in the culture medium must also be removed using a reducing agent, such as cysteine, sodium thioglycolate or sodium sulfide, or by heat treatment or exposure to nitrogen.

The concentration of xylose in the culture fluid may be set in accordance with the type of the microorganism used. In order to materialize the production of a sufficient quantity of substituted α-hydroxy acids, the xylose may usually be in a concentration of 0.1% by weight or more, and preferably 0.5% by weight or more. On the other hand, in order to produce fewer by-products, it may usually be in a concentration of 10% by weight or less, and preferably 5% by weight or less.

Any auxiliary carbon sources are unnecessary, and the xylose may be used as a single carbon source. As nitrogen sources, usable are organic or inorganic nitrogen sources, such as urea, ammonia, ammonium sulfate and ammonium nitrate, and natural nitrogen sources, such as corn steep liquor, peptone, meat extract and yeast extract. As inorganic salts, usable are potassium phosphate, sodium phosphate, magnesium sulfate, manganese sulfate, ferrous sulfate, potassium chloride and sodium chloride.

Fermentation temperature may usually be set at 15° C. or above, and preferably 20° C. or above, in order to materialize the production of a sufficient quantity of substituted α-hydroxy acids. On the other hand, in order to produce fewer by-products and prevent the strain from dying out, it may usually be set at 37° C. or below, and preferably 35° C. or below.

The culture fluid may also usually have a pH of approximately from 5 to 8 at a suitable temperature, which may appropriately be set in accordance with the nature of the microorganism.

Further with regard to fermentation time, which depends on the type of the microorganism, in the case of the strain HICA432, the fermentation can be completed in three days to a week, or, under selected conditions for pre-fermentation, in one to three days.

As described above, when the xylose is used as a single carbon source, the strain HICA432 does not substantially produce any lactic acid. Hence, this is advantageous when at least one of the β-phenyllactic acid and the 2-hydroxyisocaproic acid is chiefly needed.

Fourth Embodiment

The process of the fourth embodiment comprises the step of hydrolyzing a material containing hemicellulose and cellulose to obtain xylose and glucose, and the step of fermenting the xylose and glucose with a microorganism to obtain at least one substituted α-hydroxy acid represented by the formula: HO—CHR—COOH (wherein R represents a hydrocarbon group having 1 to 10 carbon atoms).

These steps are described below.

Xylose and Glucose from Hemicellulose and Cellulose

As materials containing the raw materials hemicellulose and cellulose, any commercially available hemicellulose and cellulose may be used as a matter of course, and any waste hemicellulose and waste cellulose obtained by appropriately treating waste paper, woods, such as waste wood, as well as pulp waste liquor, may also be used. Thus, the establishment of a method of synthesizing polyester from hemicellulose and cellulose can provide a new route for the recycling of waste hemicellulose and waste cellulose. In this regard, the polyester production process of the present invention is at the same time a useful method of recycling hemicellulose and cellulose.

The conversion of hemicellulose and cellulose into xylose and glucose, respectively, may be made by, e.g., a method of decomposing the hemicellulose and cellulose with enzymes, such as xylanase and cellulanase, a method of decomposing them with an acid, such as sulfuric acid or hydrochloric acid, or a method of decomposing them with supercritical water, whereby the hemicellulose and cellulose can be simultaneously decomposed.

Substituted α-Hydroxy Acid from Xylose and Glucose

The conversion of xylose and glucose into substituted α-hydroxy acids is carried out by anaerobic fermentation attributable to a microorganism. Incidentally, the production of hydroxy acids by microorganisms is disclosed in Japanese Patent Applications Laid-open No. 5-336981, No. 7-327692 and No. 2000-300284. There is, however, no specific disclosure as to any microorganisms capable of producing substituted α-hydroxy acids from xylose and glucose.

As the microorganism of the present embodiment, the same one as that in the third embodiment is used. More specifically, not the direct screening of strains capable of converting the xylose and glucose into the substituted α-hydroxy acid is used, but, as described in the first embodiment, screening was first conducted for strains capable of converting glucose into the substituted α-hydroxy acid, and then, from among the strains obtained, further screening has further been made on strains capable of converting also the xylose into the substituted α-hydroxy acid.

Then, on the strains thus obtained, the ability to produce substituted α-hydroxy acids also from xylose has been studied.

As a result, we have succeeded in obtaining the *Clostridium beijerinckii* strain HICA432 as a strain capable of producing 2-hydroxyisocaproic acid from xylose and glucose, which is a bacterium of the genus *Clostridium*, such as *Clostridium beijerinckii*.

On the *Clostridium beijerinckii* strain HICA432, FERMP-18373, thus obtained, products formed from xylose and glucose have further been analyzed to find that, in addition to the 2-hydroxyisocaproic acid as the substituted α-hydroxy acid represented by HO—CHR—COOH (R is an isobutyl group), at least lactic acid (R is a methyl group) and β-phenyllactic acid (R is a benzyl group) have been produced. Hence, a polyester can be produced from at least one of these substituted α-hydroxy acids.

Stated specifically, when the substituted α-hydroxy acids produced from xylose and glucose by the aid of the strain HICA432 are used, the polyester obtained has at least one of the repeating units represented by the above Formulas (I) to (III).

The substituted α-hydroxy acids produced from xylose and glucose by the aid of the strain HICA432 may optionally be purified in the same manner as in the Examples and in the foregoing embodiments. The structures, physical properties and so forth of the purified products thus obtained are also the same as those of the purified products obtained in the first embodiment.

The fermentation for converting the xylose and glucose into the substituted α-hydroxy acid is carried out by adding the strain to a culture fluid containing the xylose and glucose as chief carbon sources, and also containing nitrogen, phosphorus, mineral(s), vitamin(s) and so forth, added thereto as nutrients, and maintaining it under anaerobic conditions.

The above strain is an absolutely anaerobic bacterium, which dies out in the presence of oxygen, and hence the anaerobic conditions must be strictly set up. After the culture medium has been injected, the gaseous-phase portion in a culturing container, hermetically closed with a butyl rubber stopper or the like not transmitting any gases, is displaced with nitrogen, carbon dioxide, hydrogen or the like. Any oxygen in the culture medium must also be removed using a reducing agent, such as cysteine, sodium thioglycolate or sodium sulfide, or by heat treatment or exposure to nitrogen.

The concentration of xylose and glucose in the culture fluid may be set in accordance with the type of the microorganism used. In order to materialize the production of a sufficient quantity of substituted α-hydroxy acids, any one of the xylose and glucose or the total of the xylose and glucose may usually be in a concentration of 0.1% by weight or more, and preferably 0.5% by weight or more. On the other hand, in order to produce fewer by-products, it may usually be in a concentration of 10% by weight or less, and preferably 5% by weight or less.

Any auxiliary carbon sources are unnecessary, and only the xylose and glucose may be used as carbon sources. As nitrogen sources, usable are organic or inorganic nitrogen sources, such as urea, ammonia, ammonium sulfate and ammonium nitrate, and natural nitrogen sources, such as corn steep liquor, peptone, meat extract and yeast extract. As inorganic salts, usable are potassium phosphate, sodium phosphate, magnesium sulfate, manganese sulfate, ferrous sulfate, potassium chloride and sodium chloride.

Fermentation temperature may usually be set at 15° C. or above, and preferably 20° C. or above, in order to materialize the production of a sufficient quantity of substituted α-hydroxy acids. On the other hand, in order to produce fewer by-products and prevent the strain from dying out, it may usually be set at 37° C. or below, and preferably 35° C. or below.

The culture fluid may also usually have a pH of approximately from 5 to 8 at a suitable temperature, which may appropriately be set in accordance with the nature of the microorganism.

Further with regard to fermentation time, which depends on the type of the microorganism, in the case of the strain HICA432, the fermentation can be completed in three days to a week, or, under selected conditions for pre-fermentation, in one to three days.

B. The Step of Obtaining Cyclic Dimer Lactide from Substituted α-Hydroxy Acid:

The polyester may be directly produced from the substituted α-hydroxy acid obtained through the steps described in any of the first to fourth embodiments. However, prior to the step of polymerization, the substituted α-hydroxy acid may be converted into a derivative having a high polymerization activity.

For example, the substituted α-hydroxy acid may be subjected to dehydration by two molecules to effect cyclic diesterification to form a cyclic dimer lactide as a derivative of the substituted α-hydroxy acid, and thereafter this cyclic dimer lactide may be subjected to ring-opening polymerization to produce the polyester. The ring-opening polymerization commonly proceeds at a high polymerization rate, and a polyester with a high degree of polymerization can be produced.

As a method of dehydrating the substituted α-hydroxy acid by two molecules to effect cyclic diesterification, using, e.g., a reactor having a Dean-Stark trap, the substituted α-hydroxy acid and a condensation catalyst, such as p-toluene sulfonate, may be subjected to azeotropic dehydration in toluene in an atmosphere of nitrogen for 30 hours, and the water having gathered in the Dean-Stark trap may appropriately be removed to obtain the cyclic dimer lactide at a high yield.

Where lactic acid is subjected to dehydration by two molecules to effect cyclic diesterification under the above conditions, the cyclic dimer lactide obtained is a compound represented by the following Formula (I').

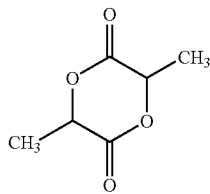

(I')

Where β-phenyllactic acid is subjected to dehydration by two molecules to effect cyclic diesterification under the above conditions, the cyclic dimer lactide obtained is a compound represented by the following Formula (II').

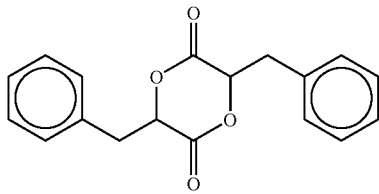

(II')

Where 2-hydroxyisocaproic acid is subjected to dehydration by two molecules to effect cyclic diesterification under the above conditions, the cyclic dimer lactide obtained is a compound represented by the following Formula (III').

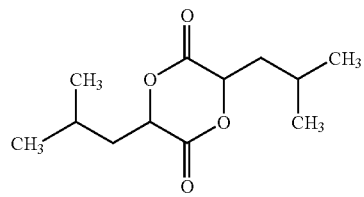

(III')

C. The Step of Obtaining Polyester from Substituted α-Hydroxy Acid:

The desired polyester may be obtained by refluxing the substituted α-hydroxy acid and a polymerization catalyst in an organic solvent, and removing outside the reaction system the water formed in the course of polymerization to make condensation polymerization proceed.

(a) Polymerization Catalyst:

In effecting the condensation polymerization of the substituted α-hydroxy acid, usable as the polymerization catalyst are, e.g., metal powders, such as tin powder and zinc powder; metal oxides, such as tin oxide, zinc oxide, magnesium oxide, titanium oxide and aluminum oxide; and metal halides, such as tin dichloride, tin tetrachloride, tin dibromide, tin tetrabromide, zinc chloride, magnesium chloride and aluminum chloride; as well as tetraphenyltin, tin octylate and p-toluene sulfonate.

The polymerization catalyst may be used in an amount of from 0.001% by weight to 10% by weight, and preferably from 0.01% by weight to 5% by weight, based on the weight of the substituted α-hydroxy acid.

(b) Polymerization Solvent:

In effecting the condensation polymerization of the substituted α-hydroxy acid, usable as the polymerization solvent are, e.g., solvents, such as toluene, xylene, mesitylene, 1,2,3,5-tetramethylbenzene, chlorobenzene, 1,2-dichlorobenzene, 1,3-dichlorobenzene, bromobenzene, 1,2-dibromobenzene, 1,3-dibromobenzene, iodobenzene, 1,2-diiodobenzene, diphenyl ether and dibenzyl ether. Any of these may be used in the form of a mixture.

The polymerization catalyst may preferably be used in such an amount that the substituted α-hydroxy acid reaches a concentration of 5% by weight to 50% by weight.

(c) Polymerization Conditions:

In effecting the condensation polymerization of the substituted α-hydroxy acid, the polymerization may be carried out at a temperature of 50° C. to 200° C., and preferably from 110° C. to 180° C., taking into account the rate of formation of a polymer and the rate of thermal decomposition of the polymer formed. The condensation polymerization reaction is usually carried out at the temperature at which the organic solvent used under normal pressure evaporates. Where an organic solvent having a high boiling point is used, the polymerization may also be carried out under reduced pressure.

In effecting the condensation polymerization of the substituted α-hydroxy acid, it may preferably be carried out in an atmosphere of an inert gas. It may also be carried out by displacing the inside of a reactor with an inert gas, or bubbling the reaction mixture with an inert gas. Also, the water formed in the course of polymerization is appropriately removed from the reactor.

The molecular weight of the polyester obtained by polymerization may be controlled by changing polymerization conditions, such as the type of the polymerization solvent, the type and amount of the polymerization catalyst, the polymerization temperature and the polymerization time. It may preferably have a weight-average molecular weight of from 5,000 to 1,000,000 in terms of polystyrene.

The polyester thus obtained may be mixed with a heat-resistant stabilizer, a weathering stabilizer, an antioxidant, an antistatic agent, a flame retardant, a lubricant, a dye, a pigment, an ultraviolet absorbent, a cross-linking agent and so forth as long as the object of the present invention can still be achieved. There are no particular limitations on the proportion in which these are mixed, which may be determined as appropriate under the circumstances.

Where the polyester is produced by carrying out the condensation polymerization in an organic solvent at a temperature lower than 200° C., it can be kept from being colored or from any impurities due to thermal decomposition. Hence, when it is used for purposes such as adhesives and coating materials, it can be dyed in any desired color, and there is an advantage in terms of the external appearance.

The polyester obtained as described above has good melt moldability, and a polyester having a weight-average molecular weight of more than 50,000 has sufficient mechanical strength. Accordingly, it is utilizable for many purposes. For example, it may be used for packaging films, bottles, cups, trays, spoons, knives, forks, trash or garbage bags and so forth.

The substituted α-hydroxy acid is also an optical isomer (chiral), and the polyester obtained by subjecting the substituted α-hydroxy acid directly to dehydration condensation polymerization also retains a chiral structure. Accordingly, the polyester may also be used as an optical material. Its uses are by no means so limited.

D. The Step of Obtaining Polyester from Cyclic Dimer Lactide:

The polyester production process described in the previous paragraph is the process of obtaining a polyester by polymerization of the substituted α-hydroxy acid. The desired polyester may also be obtained by adding a polymerization catalyst to the cyclic dimer lactide to effect a ring-opening polymerization in an atmosphere of an inert gas.

(a) Polymerization Catalyst:

In effecting the ring-opening polymerization of the cyclic dimer lactide, usable as the polymerization catalyst are, e.g., metal powders, such as tin powder and zinc powder; metal oxides, such as tin oxide, zinc oxide, magnesium oxide, titanium oxide and aluminum oxide; and metal halides, such as tin dichloride, tin tetrachloride, tin dibromide, tin tetrabromide, zinc chloride, magnesium chloride and aluminum chloride; as well as tetraphenyltin and tin octylate. Of these, tin and tin compounds have a superior catalytic activity, and these are particularly preferred.

The polymerization catalyst may be used in an amount of from 0.001% by weight to 10% by weight, and preferably from 0.01% by weight to 5% by weight, based on the weight of the cyclic dimer lactide.

(b) Polymerization Conditions:

In effecting the ring-opening polymerization of the cyclic dimer lactide, the polymerization may be carried out at a temperature of 100° C. to 200° C., and preferably from 120° C. to 180° C., taking account of the rate of formation of a polymer and the rate of thermal decomposition of the polymer formed.

In effecting the ring-opening polymerization of the cyclic dimer lactide, it may preferably be carried out in an atmosphere of an inert gas. As the inert gas, usable are, e.g., nitrogen gas and argon gas.

The molecular weight of the polyester obtained by polymerization may be controlled by changing polymerization conditions, such as the type and amount of the polymerization catalyst, the polymerization temperature and the polymerization time. It may preferably have a weight-average molecular weight of from 5,000 to 1,000,000 in terms of polystyrene.

The polyester thus obtained may be mixed with a heat-resistant stabilizer, a weathering stabilizer, an antioxidant, an antistatic agent, a flame retardant, a lubricant, a dye, a pigment, an ultraviolet absorbent, a cross-linking agent and so forth as long as the object of the present invention is achieved. There are no particular limitations on the proportion in which these are mixed, which may be determined as appropriate under the circumstances.

Where the polyester is produced by carrying out the ring-opening polymerization at a temperature lower than 200° C., it can be kept from being colored or from any impurities due to thermal decomposition. Hence, when it is used for purposes such as for adhesives and coating materials, it can be dyed in any desired color, and there is an advantage in terms of the external appearance.

The polyester obtained as described above has good melt moldability, and a polyester having a weight-average molecular weight of more than 50,000 has sufficient mechanical strength. Accordingly, it is utilizable for many purposes. For example, it may be used for packaging films, bottles, cups, trays, spoons, knives, forks, trash or garbage bags and so forth.

The present invention is described below in greater detain by giving Examples. The present invention is by no means limited to these Examples. Also, unless particularly noted, commercially available high-purity products are used as reagents and so forth.

A method for the screening of the microorganisms used in the step of obtaining the substituted α-hydroxy acid by the fermentation of glucose with microorganisms as described in the first embodiment is described first.

Screening of Microorganisms Capable of Producing 2-Hydroxyisocaproic Acid

Reducing soil positioned at a layer that is a few centimeters lower than the soil surface layer of a swamp area standing wet, films of microorganisms at drain ditch surfaces, and scum floating on the surface of still water were sampled, and these were pre-cultured in a VL culture medium (10 g/l of peptone, 5 g/l of yeast extract, 2 g/l of meat extract, 5 g/l of NaCl and 2 g/l of cysteine hydrochloride) to which 5 g/l of glucose and 5 g/l of calcium carbonate had been added.

The culture medium was injected into a vial bottle in order to provide anaerobic conditions. Thereafter, its gaseous-phase portion was displaced with nitrogen gas, and the bottle was hermetically stoppered, followed by treatment in an autoclave (121° C., 98 kPa pressure, 10 minutes), which was then opened when the sample was added. After the sample was added, the gaseous-phase portion of the vial bottle was again displaced with nitrogen gas, and the bottle was hermetically closed with a butyl rubber stopper. Thereafter, a static culture was performed, but was stirred occasionally, at 30° C. for two weeks under anaerobic conditions, and then the pre-cultured fluid was added to the above culture medium kept under anaerobic conditions by the same method as the one described above, in an amount of 1% by volume based on the volume of the culture medium.

Thereafter, a static culture was performed, but was stirred occasionally, at 30° C. for a week, and then the 2-hydroxyisocaproic acid produced in the culture fluid was subjected to methylation. The resultant 2-hydroxyisocaproic acid methyl ester was evaluated by GC-MS (gas chromatograph-gas spectroscopy). Next, the culture fluid in which the formation of 2-hydroxyisocaproic acid was recognized was sterilized, which was then diluted over several stages, with 2 g/l of an aqueous cysteine hydrochloride solution whose pH was adjusted to 7.0, and was cultured for each stage of dilution by the roll tube method. As the culture medium, a culture medium was used, which was prepared by adding 2% by weight of agar to the above culture medium.

Thereafter, a culture was performed at 30° C. for 1 week, and the developed colony was suspended in the above culture medium in a glove box filled with nitrogen gas, the culture medium being kept under anaerobic conditions by the same method as the above. Thereafter, a static culture was performed, with occasional stirring, at 30° C. for a week, and then the 2-hydroxyisocaproic acid produced in the culture fluid was subjected to methylation. The resultant 2-hydroxyisocaproic acid methyl ester was evaluated by GC-MS. The culture fluid in which a large quantity of the 2-hydroxyisocaproic acid was produced was cultured by the roll tube method in the same manner as discussed above. Then, the colony formed was separated to isolate the strain capable of producing 2-hydroxyisocaproic acid. The strain thus isolated was identified to be *Clostridium beijerinckii*, and was named the strain HICA432 (FERMP-18373).

The strain HICA432 has been ascertained to be capable of producing not only the 2-hydroxyisocaproic acid, but also lactic acid and phenyllactic acid. Accordingly, in the following, the strain HICA432 is also called a 2-hydroxyisocaproic acid productive strain, a lactic acid productive strain, and a phenyllactic acid productive strain.

The following Examples 1 to 48 concern the polyester production process comprising the step of obtaining the substituted α-hydroxy acid by the fermentation of glucose with a microorganism, described in the first embodiment. As the microorganism, the 2-hydroxyisocaproic acid productive strain, strain HICA432, was used in all Examples.

EXAMPLE 1

370 parts by weight of cellulose (KC FLOCK W-100, trade name; available from Nippon Seishi K.K.) was introduced into 11,050 parts by weight of an enzyme solution, and these were stirred at 45° C. for 8 hours. As the enzyme solution, used was a solution prepared by dissolving 37 parts by weight of cellulase (MEISELASE, trade name; available from Meiji Seika Kaisha, Ltd.) in 11,000 parts by weight of an aqueous acetic acid/sodium acetate solution (pH 4.5). After the reaction was completed, 735 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 220 parts by weight of glucose.

The $^{13}$C-NMR (100 MHz; internal standard reference material: TMS (tetramethylsilane), DMSO (dimethyl sulfoxide)-$d_6$) of the glucose obtained was measured with FT-NMR DPX400, manufactured by Bruker Co. Its chemical shifts δ (ppm) were as follows:
α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

220 parts by weight of this glucose was mixed with 12,100 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 121 parts by weight of a pre-culture fluid of 2-hydroxyisocaproic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure. Thereafter, the remaining solid content was heated under reduced pressure. The sublimated gas was cooled and the precipitated solid matter was collected to obtain 10 parts by weight of 2-hydroxyisocaproic acid.

The $^{13}$C-NMR (100 MHz, TMS, CDCl$_3$) of the 2-hydroxyisocaproic acid thus obtained was measured to obtain the results as follows: (δ/ppm); 180.25, 68.95, 43.16, 24.45, 23.20, 21.42. From these measurement results, it was ascertained that the desired 2-hydroxyisocaproic acid was obtained.

Its stereostructure was also evaluated using an optically active column (CYCLODEX-B, trade name; available from J & W Scientific Co.). As a result, it was ascertained that the 2-hydroxyisocaproic acid obtained was in the L-form.

Using a reactor having a Dean-Stark trap, 10 parts by weight of the 2-hydroxyisocaproic acid and 0.02 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 40 hours, and the aliphatic polyester obtained had a weight-average molecular weight of 90,000.

Its $^{13}$C-NMR (100 MHz, TMS, CDCl$_3$) was also measured to obtain the results (δ/ppm) of 169.78, 71.38, 39.33, 24.53, 23.00, 21.43. Thus, it was ascertained that the desired aliphatic polyester was synthesized.

The aliphatic polyester thus obtained, having a weight-average molecular weight of 90,000, was dissolved in chloroform. From the solution obtained, a film was formed by casting. The formed film was colorless and had the following physical properties.
Thickness: 38 to 39 μm
Tensile strength: 48 MPa (yield), 48 MPa (breaking)
Elongation: 5%

EXAMPLE 2

Using 2-hydroxyisocaproic acid obtained through the same procedure as in Example 1, an aliphatic polyester was synthesized. Using the reactor having a Dean-Stark trap, 10 parts by weight of the 2-hydroxyisocaproic acid and 0.02 part by weight of zinc chloride were put into it and 100 parts by weight of 1,3-dichlorobenzene was added thereto to effect azeotropic dehydration in an atmosphere of nitrogen, and the water having gathered in the Dean-Stark trap was appropriately removed. The polymerization time was 45 hours, and the aliphatic polyester obtained had a weight-average molecular weight of 140,000.

The aliphatic polyester thus obtained, having a weight-average molecular weight of 140,000, was dissolved in chloroform. From the solution obtained, a film was formed by casting. The formed film was colorless and had the following physical properties.
Thickness: 39 to 40 μm
Tensile strength: 57 MPa (yield), 56 MPa (breaking)
Elongation: 9%

EXAMPLE 3

Reclaimed paper for PPC (EN-500, A4, available from CANON SALES CO., INC.) having been used (a copy had been taken on one side using a copying machine) was cut in a size of 5 mm square, and 380 parts by weight of the same was introduced into 11,300 parts by weight of an enzyme solution, followed by stirring at 45° C. for 10 hours. As the enzyme solution, used was a solution prepared by dissolving 40 parts by weight of cellulase (MEISELASE TP60, trade name; available from Meiji Seika Kaisha, Ltd.) in 11,200 parts by weight of an aqueous acetic acid/sodium acetate solution (pH 4.5). After the reaction was completed, 750 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 210 parts by weight of glucose.

210 parts by weight of this glucose was mixed with 11,600 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 116 parts by weight of a pre-culture fluid of 2-hydroxy-isocaproic acid productive strain HICA432 isolated in the manner as described previously was added thereto by means of a syringe when the bottle was kept hermetically stoppered, followed by a static culture at 30° C. for 3 days. Thereafter, the procedure in Example 1 was repeated to collect 9 parts by weight of 2-hydroxyisocaproic acid.

Its $^{13}$C-NMR was measured to find that the same spectrum as that in Example 1 was obtained, and it was ascertained that the desired 2-hydroxyisocaproic acid was obtained.

Using the reactor having a Dean-Stark trap, 9 parts by weight of the 2-hydroxyisocaproic acid and 0.018 part by weight of tin octylate were put into it and 90 parts by weight of mesitylene was added thereto to effect azeotropic dehydration in an atmosphere of nitrogen, and the water having gathered in the Dean-Stark trap was appropriately removed. The polymerization time was 40 hours, and the aliphatic polyester obtained had a weight-average molecular weight of 50,000.

Its $^{13}$C-NMR was also measured to find that the same spectrum as that in Example 1 was obtained, and it was ascertained that the desired aliphatic polyester was obtained.

The aliphatic polyester thus obtained, having a weight-average molecular weight of 50,000, was dissolved in chloroform. From the solution obtained, a film was formed by casting. The formed film was colorless and had the following physical properties.
Thickness: 38 to 39 μm
Tensile strength: 20 MPa (yield), 20 MPa (breaking)
Elongation: 3%

EXAMPLE 4

Using 2-hydroxyisocaproic acid obtained through the same procedure as in Example 3, an aliphatic polyester was synthesized. Using the reactor having a Dean-Stark trap, 9 parts by weight of the 2-hydroxyisocaproic acid and 0.02 part by weight of tin powder were put into it and 100 parts by weight of diphenyl ether was added thereto to effect azeotropic dehydration at 130° C./12 mmHg, and the water having gathered in the Dean-Stark trap was appropriately removed. The polymerization time was 48 hours, and the aliphatic polyester obtained had a weight-average molecular weight of 190,000.

The aliphatic polyester thus obtained, having a weight-average molecular weight of 190,000, was dissolved in chloroform. From the solution obtained, a film was formed by casting. The formed film was colorless and had the following physical properties.
Thickness: 39 to 40 μm
Tensile strength: 69 MPa (yield), 67 MPa (breaking)
Elongation: 13%

EXAMPLE 5

370 parts by weight of cellulose (KC FLOCK W-100, trade name; available from Nippon Seishi K.K.) was introduced into 11,050 parts by weight of an enzyme solution, and these were stirred at 45° C. for 8 hours. As the enzyme solution, used was a solution prepared by dissolving 37 parts by weight of cellulase (MEISELASE, trade name; available from Meiji Seika Kaisha, Ltd.) in 11,000 parts by weight of an aqueous acetic acid/sodium acetate solution (pH 4.5). After the reaction was completed, 735 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 220 parts by weight of glucose.

The $^{13}$C-NMR (100 MHz, TMS, DMSO-$d_6$) of the glucose obtained was measured with FT-NMR DPX400, manufactured by Bruker Co. Its chemical shifts δ (ppm) were as follows:
α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

220 parts by weight of this glucose was mixed with 12,100 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the treated culture medium was cooled to 30° C., and 121 parts by weight of a pre-culture fluid of 2-hydroxyisocaproic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure. Thereafter, the solid content having remained was heated under reduced pressure. The gas having sublimated was cooled and the solid matter having precipitated was collected to obtain 10 parts by weight of 2-hydroxyisocaproic acid.

The $^{13}$C-NMR (100 MHz, TMS, CDCl$_3$) of this 2-hydroxyisocaproic acid was measured to obtain the results (δ/ppm) of 180.25, 68.95, 43.16, 24.45, 23.20, 21.42. Thus, it was ascertained that the desired 2-hydroxyisocaproic acid was obtained.

Using the reactor having a Dean-Stark trap, 10 parts by weight of the 2-hydroxyisocaproic acid and 0.2 part by weight of p-toluenesulfonic acid were put into it and 600 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The residue formed was recrystallized from ether to obtain 8.2 parts by weight of a cyclic dimer lactide.

The $^{13}$C-NMR (100 MHz, TMS, CDCl$_3$) of the cyclic dimer lactide obtained was measured to obtain the results (δ/ppm) of 167.33, 74.14, 38.87, 23.89, 23.03, 21.33. Thus, it was ascertained that the desired cyclic dimer lactide was obtained.

8.2 parts by weight of the cyclic dimer lactide and 0.01 part by weight of tin chloride were heated at 150° C. for 12 hours in an atmosphere of nitrogen to effect ring-opening polymerization. The aliphatic polyester thus obtained had a weight-average molecular weight of 180,000.

The $^{13}$C-NMR (100 MHz, TMS, CDCl$_3$) of this aliphatic polyester was measured to obtain the results (δ/ppm) of 169.78, 71.38, 39.33, 24.53, 23.00, 21.43. Thus, it was ascertained that the desired aliphatic polyester was synthesized.

The aliphatic polyester thus obtained, having a weight-average molecular weight of 180,000, was dissolved in chloroform. From the solution obtained, a film was formed by casting. The formed film was colorless and had the following physical properties.
Thickness: 38 to 39 μm
Tensile strength: 68 MPa (yield), 68 MPa (breaking)
Elongation: 13%

EXAMPLE 6

Using a cyclic dimer lactide obtained through the same procedure as in Example 5, an aliphatic polyester was synthesized. That is, 8.2 parts by weight of the cyclic dimer lactide and 0.01 part by weight of zinc chloride were heated at 120° C. for 5 hours in an atmosphere of nitrogen to effect ring-opening polymerization. The aliphatic polyester thus obtained had a weight-average molecular weight of 50,000. Its $^{13}$C-NMR was measured to find that the same spectrum as that in Example 5 was obtained, and it was ascertained that the desired aliphatic polyester was obtained.

The aliphatic polyester thus obtained, having a weight-average molecular weight of 50,000, was dissolved in chloroform. From the solution obtained, a film was formed by casting. The formed film was colorless and had the following physical properties.
Thickness: 39 to 40 μm
Tensile strength: 29 MPa (yield), 29 MPa (breaking)
Elongation: 4%

EXAMPLE 7

Reclaimed paper for PPC (EN-500, A4, available from CANON SALES CO., INC.) having been used (a copy had been taken on one side using a copying machine) was cut in a size of 5 mm square, and 380 parts by weight of the same was introduced into 11,300 parts by weight of an enzyme solution, followed by stirring at 45° C. for 10 hours. As the enzyme solution, used was a solution prepared by dissolving 40 parts by weight of cellulase (MEISELASE TP60, trade name; available from Meiji Seika Kaisha, Ltd.) in 11,200 parts by weight of an aqueous acetic acid/sodium acetate solution (pH 4.5). After the reaction was completed, 750 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 210 parts by weight of glucose.

210 parts by weight of this glucose was mixed with 11,600 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 116 parts by weight of a pre-culture fluid of 2-hydroxyisocaproic acid productive strain HICA432 isolated in the manner as described previously was added thereto by means of a syringe when the bottle was kept hermetically stoppered, followed by a static culture at 30° C. for 3 days. Thereafter, the procedure in Example 5 was repeated to collect 9 parts by weight of 2-hydroxyisocaproic acid.

Its $^{13}$C-NMR was measured to find that the same spectrum as that in Example 5 was obtained, and it was ascertained that the desired 2-hydroxyisocaproic acid was obtained. Then, 9 parts by weight of the 2-hydroxyisocaproic acid obtained was treated through the same procedure as in Example 5 to obtain 7.4 parts by weight of a cyclic dimer lactide.

7.4 parts by weight of the cyclic dimer lactide and 0.008 part by weight of tin octylate were heated at 180° C. for 30 hours in an atmosphere of nitrogen to effect ring-opening polymerization. The aliphatic polyester thus obtained had a weight-average molecular weight of 680,000. Its $^{13}$C-NMR was measured to find that the same spectrum as that in Example 5 was obtained, and it was ascertained that the desired aliphatic polyester was obtained.

The aliphatic polyester thus obtained, having a weight-average molecular weight of 680,000, was dissolved in chloroform. From the solution obtained, a film was formed by casting. The formed film was colorless and had the following physical properties.

Thickness: 38 to 39 μm
Tensile strength: 98 MPa (yield), 98 MPa (breaking)
Elongation: 30%

EXAMPLE 8

Using a cyclic dimer lactide obtained through the same procedure as in Example 7, an aliphatic polyester was synthesized. That is, 7.4 parts by weight of the cyclic dimer lactide and 0.007 part by weight of tin powder were heated at 160° C. for 18 hours in an atmosphere of nitrogen to effect ring-opening polymerization. The aliphatic polyester thus obtained had a weight-average molecular weight of 390,000. Its $^{13}$C-NMR was measured to find that the same spectrum as that in Example 5 was obtained, and it was ascertained that the desired aliphatic polyester was obtained.

The aliphatic polyester thus obtained, having a weight-average molecular weight of 390,000, was dissolved in chloroform. From the solution obtained, a film was formed by casting. The formed film was colorless and had the following physical properties.
Thickness: 39 to 40 μm
Tensile strength: 88 MPa (yield), 87 MPa (breaking)
Elongation: 22%

EXAMPLE 9

370 parts by weight of cellulose (KC FLOCK W-100, trade name; available from Nippon Seishi K.K.) was introduced into 11,050 parts by weight of an enzyme solution, and these were stirred at 45° C. for 8 hours. As the enzyme solution, used was a solution prepared by dissolving 37 parts by weight of cellulase (MEISELASE, trade name; available from Meiji Seika Kaisha, Ltd.) in 11,000 parts by weight of an aqueous acetic acid/sodium acetate solution (pH 4.5). After the reaction was completed, 735 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 220 parts by weight of glucose.

The $^{13}$C-NMR (100 MHz, TMS, DMSO-$d_6$) of the glucose obtained was measured with FT-NMR DPX400, manufactured by Bruker Co. Its chemical shifts δ (ppm) were as follows:
α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

220 parts by weight of this glucose was mixed with 12,100 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 121 parts by weight of a pre-culture fluid of phenyllactic acid productive strain HICA432 isolated in the manner as described previously was added thereto by means of a syringe when the bottle was kept hermetically stoppered, followed by a static culture at 30° C. for 3 days.

Thereafter, the culture fluid was filtered, and the water and volatile components of the filtrate obtained were evaporated off under normal-temperature reduced pressure, followed by purification to obtain 10 parts by weight of phenyllactic acid. The $^{13}$C-NMR (100 MHz, TMS, CDCl$_3$) of the phenyllactic acid thus obtained was measured to obtain the results (δ/ppm) of 177.92, 137.63, 130.30, 129.46, 127.82, 72.05, 40.38, and it was ascertained that the desired phenyllactic acid was obtained.

Its stereostructure was also evaluated using an optically active column (CYCLODEX-B, trade name; available from J & W Scientific Co.). As a result, it was ascertained that the phenyllactic acid obtained was in the L-form.

Using the reactor having a Dean-Stark trap, 10 parts by weight of the phenyllactic acid and 0.018 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 44 hours, and the aromatic polyester obtained had a weight-average molecular weight of 180,000.

The aromatic polyester thus obtained, having a weight-average molecular weight of 180,000, was dissolved in chloroform. From the solution obtained, a film was formed by casting. The formed film was colorless and had the following physical properties.
Thickness: 38 to 39 μm
Tensile strength: 69 MPa (yield), 69 MPa (breaking)
Elongation: 12%

EXAMPLE 10

Using phenyllactic acid obtained through the same procedure as in Example 9, an aromatic polyester was synthesized. Using the reactor having a Dean-Stark trap, 10 parts by weight of the phenyllactic acid and 0.02 part by weight of zinc chloride were put into it and 100 parts by weight of 1,3-dichlorobenzene was added thereto to effect azeotropic dehydration in an atmosphere of nitrogen, and the water having gathered in the Dean-Stark trap was appropriately removed. The polymerization time was 16 hours, and the aromatic polyester obtained had a weight-average molecular weight of 30,000.

The aromatic polyester thus obtained, having a weight-average molecular weight of 30,000, was dissolved in chloroform. From the solution obtained, a film was formed by casting. The formed film was colorless and had the following physical properties.
Thickness: 39 to 40 μm
Tensile strength: 20 MPa (yield), 19 MPa (breaking)
Elongation: 2%

EXAMPLE 11

Reclaimed paper for PPC (EN-500, A4, available from CANON SALES CO., INC.) having been used (a copy had been taken on one side using a copying machine) was cut in a size of 5 mm square, and 380 parts by weight of the same was introduced into 11,300 parts by weight of an enzyme solution, followed by stirring at 45° C. for 10 hours. As the enzyme solution, used was a solution prepared by dissolving 40 parts by weight of cellulase (MEISELASE TP60, trade name; available from Meiji Seika Kaisha, Ltd.) in 11,200 parts by weight of an aqueous acetic acid/sodium acetate solution (pH 4.5). After the reaction was completed, 750 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 210 parts by weight of glucose.

210 parts by weight of this glucose was mixed with 11,600 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 116 parts by weight of a pre-culture fluid of phenyllactic acid productive strain HICA432 isolated in the manner as described previously was added thereto by means of a syringe when the bottle was kept hermetically stoppered, followed by a static culture at 30° C. for 3 days. Thereafter, the procedure in Example 1 was repeated to collect 9 parts by weight of phenyllactic acid.

Its $^{13}$C-NMR was measured to find that the same spectrum as that in Example 9 was obtained, and it was ascertained that the desired phenyllactic acid was obtained.

Using the reactor having a Dean-Stark trap, 9 parts by weight of the phenyllactic acid and 0.016 part by weight of tin oxide were put into it and 90 parts by weight of mesitylene was added thereto to effect azeotropic dehydration in an atmosphere of nitrogen, and the water having gathered in the Dean-Stark trap was appropriately removed. The polymerization time was 40 hours, and the aromatic polyester obtained had a weight-average molecular weight of 90,000.

The aromatic polyester thus obtained, having a weight-average molecular weight of 90,000, was dissolved in chloroform. From the solution obtained, a film was formed by casting. The formed film was colorless and had the following physical properties.
Thickness: 38 to 39 μm
Tensile strength: 49 MPa (yield), 49 MPa (breaking)
Elongation: 5%

EXAMPLE 12

Using phenyllactic acid obtained through the same procedure as in Example 11, an aromatic polyester was synthesized. Using the reactor having a Dean-Stark trap, 9 parts by weight of the phenyllactic acid and 0.015 part by weight of tin powder were put into it and 100 parts by weight of diphenyl ether was added thereto to effect azeotropic dehydration at 130° C./12 mmHg, and the water having gathered in the Dean-Stark trap was appropriately removed. The polymerization time was 48 hours, and the aromatic polyester obtained had a weight-average molecular weight of 250,000.

The aromatic polyester thus obtained, having a weight-average molecular weight of 250,000, was dissolved in chloroform. From the solution obtained, a film was formed by casting. The formed film was colorless and had the following physical properties.
Thickness: 39 to 40 μm
Tensile strength: 82 MPa (yield), 81 MPa (breaking)
Elongation: 18%

EXAMPLE 13

370 parts by weight of cellulose (KC FLOCK W-100, trade name; available from Nippon Seishi K.K.) was introduced into 11,050 parts by weight of an enzyme solution, and these were stirred at 45° C. for 8 hours. As the enzyme solution, used was a solution prepared by dissolving 37 parts by weight of cellulase (MEISELASE, trade name; available from Meiji Seika Kaisha, Ltd.) in 11,000 parts by weight of an aqueous acetic acid/sodium acetate solution (pH 4.5). After the reaction was completed, 735 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 220 parts by weight of glucose.

The $^{13}$C-NMR (100 MHz, TMS, DMSO-$d_6$) of the glucose obtained was measured with FT-NMR DPX400, manufactured by Bruker Co. Its chemical shifts δ (ppm) were as follows:
α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

220 parts by weight of this glucose was mixed with 12,100 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 121 parts by weight of a pre-culture fluid of phenyllactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by purification to obtain 10 parts by weight of phenyllactic acid.

The $^{13}$C-NMR (100 MHz, TMS, CDCl$_3$) of this phenyllactic acid was measured to obtain the results (δ/ppm) of 177.92, 137.63, 130.30, 129.46, 127.82, 72.05, 40.38, and it was ascertained that the desired phenyllactic acid was obtained.

Using the reactor having a Dean-Stark trap, 10 parts by weight of the phenyllactic acid and 0.2 part by weight of p-toluenesulfonic acid were put into it and 600 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The formed residue was recrystallized from ether to obtain 8.7 parts by weight of a cyclic dimer lactide.

8.7 parts by weight of the cyclic dimer lactide and 0.01 part by weight of tin chloride were heated at 160° C. for 10 hours in an atmosphere of nitrogen to effect ring-opening polymerization. The aromatic polyester thus obtained had a weight-average molecular weight of 190,000.

The aromatic polyester thus obtained, having a weight-average molecular weight of 190,000, was dissolved in chloroform. From the solution obtained, a film was formed by casting. The formed film was colorless and had the following physical properties.
Thickness: 39 to 40 μm
Tensile strength: 69 MPa (yield), 69 MPa (breaking)
Elongation: 12%

EXAMPLE 14

Using a cyclic dimer lactide obtained through the same procedure as in Example 13, an aromatic polyester was synthesized. That is, 8.7 parts by weight of the cyclic dimer lactide and 0.01 part by weight of zinc chloride were heated at 120° C. for 5 hours in an atmosphere of nitrogen to effect ring-opening polymerization. The aromatic polyester thus obtained had a weight-average molecular weight of 50,000.

The aromatic polyester thus obtained, having a weight-average molecular weight of 50,000, was dissolved in chloroform. From the solution obtained, a film was formed by casting. The formed film was colorless and had the following physical properties.
Thickness: 40 to 41 μm
Tensile strength: 31 MPa (yield), 30 MPa (breaking)
Elongation: 3%

EXAMPLE 15

Reclaimed paper for PPC (EN-500, A4, available from CANON SALES CO., INC.) having been used (a copy had been taken on one side using a copying machine) was cut in a size of 5 mm square, and 380 parts by weight of the same was introduced into 11,300 parts by weight of an enzyme solution, followed by stirring at 45° C. for 10 hours. As the enzyme solution, used was a solution prepared by dissolving 40 parts by weight of cellulase (MEISELASE TP60, trade name; available from Meiji Seika Kaisha, Ltd.) in 11,200 parts by weight of an aqueous acetic acid/sodium acetate solution (pH 4.5). After the reaction was completed, 750 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 210 parts by weight of glucose.

210 parts by weight of this glucose was mixed with 11,600 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 116 parts by weight of a pre-culture fluid of phenyllactic acid productive strain HICA432 isolated in the manner as described previously was added thereto by means of a syringe when the bottle was kept hermetically stoppered, followed by a static culture at 30° C. for 3 days. Thereafter, the procedure in Example 13 was repeated to collect 9 parts by weight of phenyllactic acid.

Its $^{13}$C-NMR was measured to find that the same spectrum as that in Example 13 was obtained, and it was ascertained that the desired phenyllactic acid was obtained.

9 parts by weight of the phenyllactic acid obtained was treated through the same procedure as in Example 13 to obtain 7.8 parts by weight of a cyclic dimer lactide.

7.8 parts by weight of the cyclic dimer lactide and 0.007 part by weight of tin octylate were heated at 180° C. for 33 hours in an atmosphere of nitrogen to effect ring-opening polymerization. The aromatic polyester thus obtained had a weight-average molecular weight of 700,000.

The aromatic polyester thus obtained, having a weight-average molecular weight of 700,000, was dissolved in chloroform. From the solution obtained, a film was formed by casting. The formed film was colorless and had the following physical properties.
Thickness: 39 to 40 μm
Tensile strength: 98 MPa (yield), 98 MPa (breaking)
Elongation: 25%

EXAMPLE 16

Using a cyclic dimer lactide obtained through the same procedure as in Example 15, an aromatic polyester was synthesized. That is, 7.8 parts by weight of the cyclic dimer lactide and 0.006 part by weight of tin powder were heated at 160° C. for 18 hours in an atmosphere of nitrogen to effect ring-opening polymerization. The aromatic polyester thus obtained had a weight-average molecular weight of 380,000.

The aromatic polyester thus obtained, having a weight-average molecular weight of 380,000, was dissolved in chloroform. From the solution obtained, a film was formed by casting. The formed film was colorless and had the following physical properties.
Thickness: 38 to 39 μm
Tensile strength: 87 MPa (yield), 86 MPa (breaking)
Elongation: 16%

EXAMPLE 17

340 parts by weight of cellulose (KC FLOCK W-100, trade name; available from Nippon Seishi K.K.) was introduced into 10,250 parts by weight of an enzyme solution, and these were stirred at 45° C. for 8 hours. As the enzyme solution, used was a solution prepared by dissolving 34 parts by weight of cellulase (MEISELASE, trade name; available from Meiji Seika Kaisha, Ltd.) in 10,000 parts by weight of an aqueous acetic acid/sodium acetate solution (pH 4.5). After the reaction was completed, 670 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 200 parts by weight of glucose.

The $^{13}$C-NMR (100 MHz, TMS, DMSO-$d_6$) of the glucose obtained was measured with FT-NMR DPX400, manufactured by Bruker Co. Its chemical shifts δ (ppm) were as follows:
α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

200 parts by weight of this glucose was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of 2-hydroxyisocaproic acid/lactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 10 parts by weight of 2-hydroxyisocaproic acid and 12 parts by weight of lactic acid was obtained.

Its $^1$H-NMR (400 MHz, TMS, DMSO-$d_6$) was measured to obtain the results ($\delta$/ppm) as follows:

2-hydroxyisocaproic acid: 0.88 (t, 6H), 1.37 to 1.48 (m, 2H), 1.72 to 1.82 (m, 1H), 3.94 (dd, 1H);

lactic acid: 1.25 (d, J=6.8 Hz, 3H), 4.07 (q, J=6.8 Hz, 1H).

Its $^{13}$C-NMR (100 MHz, TMS, DMSO-$d_6$) was also measured to obtain the results ($\delta$/ppm) as follows:

2-hydroxyisocaproic acid: 21.43, 23.12, 23.84, 42.84, 68.07, 176.23;

lactic acid: 20.39, 65.82, 176.42.

The stereostructure of the 2-hydroxyisocaproic acid was also evaluated using an optically active column (CYCLODEX-B, trade name; available from J & W Scientific Co.). As a result, it was ascertained that the 2-hydroxyisocaproic acid obtained was in the L-form.

Meanwhile, the stereostructure of the lactic acid was evaluated using an optically active column (RESTEK Column 13113, trade name; available from Uniflex Co.). As a result, it was ascertained that the lactic acid obtained was in the DL-form.

Using the reactor having a Dean-Stark trap, 10 parts by weight of the 2-hydroxyisocaproic acid, 12 parts by weight of the lactic acid and 0.044 part by weight of tin dichloride were put into it and 220 parts by weight of mesitylene was added thereto to effect azeotropic dehydration in an atmosphere of nitrogen, and the water having gathered in the Dean-Stark trap was appropriately removed. The polymerization time was 40 hours, and the aliphatic polyester copolymer obtained had a weight-average molecular weight of 170,000.

Its $^{13}$C-NMR (100 MHz, TMS, CDCl$_3$) was measured to obtain the results ($\delta$/ppm) of 16.66, 21.43, 22.99, 24.55, 39.30, 68.97, 71.37, 169.51, 169.76. Thus, it was ascertained that the desired aliphatic polyester copolymer was synthesized.

The aliphatic polyester copolymer thus obtained, having a weight-average molecular weight of 170,000, was dissolved in chloroform. From the solution obtained, a film was formed by casting. The formed film was colorless and had the following physical properties.

Thickness: 38 to 39 μm
Tensile strength: 61 MPa (yield), 59 MPa (breaking)
Elongation: 14%

EXAMPLE 18

Using 2-hydroxyisocaproic acid and lactic acid obtained through the same procedure as in Example 17, an aliphatic polyester copolymer was synthesized. Using the reactor having a Dean-Stark trap, 10 parts by weight of the 2-hydroxyisocaproic acid, 12 parts by weight of the lactic acid and 0.04 part by weight of zinc powder were put into it and 200 parts by weight of 1,3-dichlorobenzene was added thereto to effect azeotropic dehydration in an atmosphere of nitrogen, and the water having gathered in the Dean-Stark trap was appropriately removed. The polymerization time was 38 hours, and the aliphatic polyester copolymer obtained had a weight-average molecular weight of 100,000.

Its $^{13}$C-NMR was also measured to find that the same spectrum as that in Example 17 was obtained, and it was ascertained that the desired aliphatic polyester copolymer was synthesized.

The aliphatic polyester copolymer thus obtained, having a weight-average molecular weight of 100,000, was dissolved in chloroform. From the solution obtained, a film was formed by casting. The formed film was colorless and had the following physical properties.

Thickness: 39 to 40 μm
Tensile strength: 49 MPa (yield), 49 MPa (breaking)
Elongation: 6%

EXAMPLE 19

Reclaimed paper for PPC (EN-500, A4, available from CANON SALES CO., INC.) having been used (a copy had been taken on one side using a copying machine) was cut in a size of 5 mm square, and 500 parts by weight of the same was introduced into 15,050 parts by weight of an enzyme solution, followed by stirring at 45° C. for 10 hours. As the enzyme solution, used was a solution prepared by dissolving 50 parts by weight of cellulase (MEISELASE TP60, trade name; available from Meiji Seika Kaisha, Ltd.) in 15,000 parts by weight of an aqueous acetic acid/sodium acetate solution (pH 4.5). After the reaction was completed, 1,000 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 280 parts by weight of glucose.

280 parts by weight of this glucose was mixed with 15,400 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 154 parts by weight of a pre-culture fluid of 2-hydroxyisocaproic acid/lactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 13 parts by weight of 2-hydroxyisocaproic acid and 16 parts by weight of lactic acid was obtained.

Using the reactor having a Dean-Stark trap, 13 parts by weight of the 2-hydroxyisocaproic acid, 16 parts by weight of the lactic acid and 0.058 part by weight of tin octylate were put into it and 290 parts by weight of mesitylene was added thereto to effect azeotropic dehydration in an atmosphere of nitrogen, and the water having gathered in the Dean-Stark trap was appropriately removed. The polymerization time was 36 hours, and the aliphatic polyester copolymer obtained had a weight-average molecular weight of 60,000.

Its $^{13}$C-NMR was also measured to find that the same spectrum as that in Example 17 was obtained, and it was ascertained that the desired aliphatic polyester copolymer was synthesized.

The aliphatic polyester copolymer thus obtained, having a weight-average molecular weight of 60,000, was dissolved in chloroform. From the solution obtained, a film was formed by casting. The formed film was colorless and had the following physical properties.
Thickness: 38 to 39 μm
Tensile strength: 22 MPa (yield), 22 MPa (breaking)
Elongation: 3%

EXAMPLE 20

Using 2-hydroxyisocaproic acid and lactic acid obtained through the same procedure as in Example 19, an aliphatic polyester copolymer was synthesized. Using the reactor having a Dean-Stark trap, 13 parts by weight of the 2-hydroxyisocaproic acid, 16 parts by weight of the lactic acid and 0.052 part by weight of tin powder were put into it and 320 parts by weight of diphenyl ether was added thereto to effect azeotropic dehydration at 130° C./12 mmHg, and the water having gathered in the Dean-Stark trap was appropriately removed. The polymerization time was 48 hours, and the aliphatic polyester copolymer obtained had a weight-average molecular weight of 290,000.

Its $^{13}$C-NMR was also measured to find that the same spectrum as that in Example 17 was obtained, and it was ascertained that the desired aliphatic polyester copolymer was synthesized.

The aliphatic polyester copolymer thus obtained, having a weight-average molecular weight of 290,000, was dissolved in chloroform. From the solution obtained, a film was formed by casting. The formed film was colorless and had the following physical properties.
Thickness: 39 to 40 μm
Tensile strength: 74 MPa (yield), 73 MPa (breaking)
Elongation: 23%

EXAMPLE 21

200 parts by weight of glucose obtained through the same procedure as in Example 17 was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with a mixed gas of 98% of nitrogen and 2% of oxygen to bring the inside of the bottle into a slightly aerobic state, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of 2-hydroxyisocaproic acid/lactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 4 parts by weight of 2-hydroxyisocaproic acid and 18 parts by weight of lactic acid was obtained.

Using the reactor having a Dean-Stark trap, 4 parts by weight of the 2-hydroxyisocaproic acid, 18 parts by weight of the lactic acid and 0.04 part by weight of tin oxide were put into it and 210 parts by weight of bromobenzene was added thereto to effect azeotropic dehydration in an atmosphere of nitrogen, and the water having gathered in the Dean-Stark trap was appropriately removed. The polymerization time was 45 hours, and the aliphatic polyester copolymer obtained had a weight-average molecular weight of 220,000.

Its $^{13}$C-NMR was also measured to find that the same spectrum as that in Example 17 was obtained, and it was ascertained that the desired aliphatic polyester copolymer was synthesized.

The aliphatic polyester copolymer thus obtained, having a weight-average molecular weight of 220,000, was dissolved in chloroform. From the solution obtained, a film was formed by casting. The formed film was colorless and had the following physical properties.
Thickness: 37 to 38 μm
Tensile strength: 69 MPa (yield), 67 MPa (breaking)
Elongation: 18%

EXAMPLE 22

280 parts by weight of glucose obtained through the same procedure as in Example 19 was cultured in the same manner as in Example 21. Thereafter, the culture fluid was filtered, and the water and volatile components of the filtrate obtained were evaporated off under normal-temperature reduced pressure, followed by NMR analysis. As a result, it was ascertained that a mixture of 5 parts by weight of 2-hydroxyisocaproic acid and 16 parts by weight of lactic acid was obtained.

Using the reactor having a Dean-Stark trap, 5 parts by weight of the 2-hydroxyisocaproic acid, 16 parts by weight of the lactic acid and 0.038 part by weight of p-toluenesulfonic acid were put into it and 200 parts by weight of 1,2-dichlorobenzene was added thereto to effect azeotropic dehydration in an atmosphere of nitrogen, and the water having gathered in the Dean-Stark trap was appropriately removed. The polymerization time was 32 hours, and the aliphatic polyester copolymer obtained had a weight-average molecular weight of 40,000.

Its $^{13}$C-NMR was also measured to find that the same spectrum as that in Example 17 was obtained, and it was ascertained that the desired aliphatic polyester copolymer was synthesized.

The aliphatic polyester copolymer thus obtained, having a weight-average molecular weight of 40,000, was dissolved in chloroform. From the solution obtained, a film was formed by casting. The formed film was colorless and had the following physical properties.
Thickness: 40 to 41 μm
Tensile strength: 19 MPa (yield), 19 MPa (breaking)
Elongation: 2%

EXAMPLE 23

340 parts by weight of cellulose (KC FLOCK W-100, trade name; available from Nippon Seishi K.K.) was introduced into 10,250 parts by weight of an enzyme solution, and these were stirred at 45° C. for 8 hours. As the enzyme solution, used was a solution prepared by dissolving 34 parts by weight of cellulase (MEISELASE, trade name; available from Meiji Seika Kaisha, Ltd.) in 10,000 parts by weight of an aqueous acetic acid/sodium acetate solution (pH 4.5). After the reaction was completed, 670 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 200 parts by weight of glucose.

The $^{13}$C-NMR (100 MHz, TMS, DMSO-$d_6$) of the glucose obtained was measured with FT-NMR DPX400, manufactured by Bruker Co. Its chemical shifts δ (ppm) were as follows:
α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

200 parts by weight of this glucose was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of 2-hydroxyisocaproic acid/phenyllactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 10 parts by weight of 2-hydroxyisocaproic acid and 12 parts by weight of phenyllactic acid was obtained.

Its $^1$H-NMR (400 MHz, TMS, DMSO-$d_6$) was measured to obtain the results (δ/ppm) as follows:
2-hydroxyisocaproic acid: 0.88 (t, 6H), 1.37 to 1.48 (m, 2H), 1.72 to 1.82 (m, 1H), 3.94 (dd, 1H);
phenyllactic acid: 2.82, 2.95, 4.16, 7.25.

The stereostructure of the 2-hydroxyisocaproic acid was also evaluated using an optically active column (CYCLO-DEX-B, trade name; available from J & W Scientific Co.). As a result, it was ascertained that the 2-hydroxyisocaproic acid obtained was in the L-form.

Meanwhile, the stereostructure of the lactic acid was evaluated using an optically active column (RESTEK Column 13113, trade name; available from Uniflex Co.). As a result, it was ascertained that the phenyllactic acid obtained was in the L-form.

Using the reactor having a Dean-Stark trap, 10 parts by weight of the 2-hydroxyisocaproic acid, 12 parts by weight of the phenyllactic acid and 0.044 part by weight of tin dichloride were put into it and 220 parts by weight of mesitylene was added thereto to effect azeotropic dehydration in an atmosphere of nitrogen, and the water having gathered in the Dean-Stark trap was appropriately removed. The polymerization time was 40 hours, and the polyester copolymer obtained had a weight-average molecular weight of 160,000.

The polyester copolymer thus obtained, having a weight-average molecular weight of 160,000, was dissolved in chloroform. From the solution obtained, a film was formed by casting. The formed film was colorless and had the following physical properties.
Thickness: 37 to 38 µm
Tensile strength: 60 MPa (yield), 60 MPa (breaking)
Elongation: 13%

EXAMPLE 24

Using 2-hydroxyisocaproic acid and phenyllactic acid obtained through the same procedure as in Example 23, a polyester copolymer was synthesized. Using the reactor having a Dean-Stark trap, 10 parts by weight of the 2-hydroxyisocaproic acid, 12 parts by weight of the phenyllactic acid and 0.04 part by weight of zinc powder were put into it and 200 parts by weight of 1,3-dichlorobenzene was added thereto to effect azeotropic dehydration in an atmosphere of nitrogen, and the water having gathered in the Dean-Stark trap was appropriately removed. The polymerization time was 38 hours, and the polyester copolymer obtained had a weight-average molecular weight of 110,000.

The polyester copolymer thus obtained, having a weight-average molecular weight of 110,000, was dissolved in chloroform. From the solution obtained, a film was formed by casting. The formed film was colorless and had the following physical properties.
Thickness: 39 to 40 µm
Tensile strength: 50 MPa (yield), 49 MPa (breaking)
Elongation: 7%

EXAMPLE 25

Reclaimed paper for PPC (EN-500, A4, available from CANON SALES CO., INC.) having been used (a copy had been taken on one side using a copying machine) was cut in a size of 5 mm square, and 500 parts by weight of the same was introduced into 15,050 parts by weight of an enzyme solution, followed by stirring at 45° C. for 10 hours. As the enzyme solution, used was a solution prepared by dissolving 50 parts by weight of cellulase (MEISELASE TP60, trade name; available from Meiji Seika Kaisha, Ltd.) in 15,000 parts by weight of an aqueous acetic acid/sodium acetate solution (pH 4.5). After the reaction was completed, 1,000 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 280 parts by weight of glucose.

280 parts by weight of this glucose was mixed with 15,400 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 154 parts by weight of a pre-culture fluid of 2-hydroxyisocaproic acid/phenyllactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 13 parts by weight of 2-hydroxyisocaproic acid and 16 parts by weight of phenyllactic acid was obtained.

Using the reactor having a Dean-Stark trap, 13 parts by weight of the 2-hydroxyisocaproic acid, 16 parts by weight of the phenyllactic acid and 0.058 part by weight of tin octylate were put into it and 290 parts by weight of mesitylene was added thereto to effect azeotropic dehydration in an atmosphere of nitrogen, and the water having gathered in the Dean-Stark trap was appropriately removed. The polymerization time was 36 hours, and the polyester copolymer obtained had a weight-average molecular weight of 70,000.

The polyester copolymer thus obtained, having a weight-average molecular weight of 70,000, was dissolved in chloroform. From the solution obtained, a film was formed by casting. The formed film was colorless and had the following physical properties.
Thickness: 40 to 41 μm
Tensile strength: 22 MPa (yield), 21 MPa (breaking)
Elongation: 4%

EXAMPLE 26

Using 2-hydroxyisocaproic acid and phenyllactic acid obtained through the same procedure as in Example 25, a polyester copolymer was synthesized. Using the reactor having a Dean-Stark trap, 13 parts by weight of the 2-hydroxyisocaproic acid, 16 parts by weight of the phenyllactic acid and 0.052 part by weight of tin powder were put into it and 320 parts by weight of diphenyl ether was added thereto to effect azeotropic dehydration at 130° C./12 mmHg, and the water having gathered in the Dean-Stark trap was appropriately removed. The polymerization time was 48 hours, and the polyester copolymer obtained had a weight-average molecular weight of 290,000.

The polyester copolymer thus obtained, having a weight-average molecular weight of 290,000, was dissolved in chloroform. From the solution obtained, a film was formed by casting. The formed film was colorless and had the following physical properties.
Thickness: 38 to 39 μm
Tensile strength: 78 MPa (yield), 77 MPa (breaking)
Elongation: 23%

EXAMPLE 27

340 parts by weight of cellulose (KC FLOCK W-100, trade name; available from Nippon Seishi K.K.) was introduced into 10,250 parts by weight of an enzyme solution, and these were stirred at 45° C. for 8 hours. As the enzyme solution, used was a solution prepared by dissolving 34 parts by weight of cellulase (MEISELASE, trade name; available from Meiji Seika Kaisha, Ltd.) in 10,000 parts by weight of an aqueous acetic acid/sodium acetate solution (pH 4.5). After the reaction was completed, 670 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 200 parts by weight of glucose.

The $^{13}$C-NMR (100 MHz; internal standard reference material: tetramethylsilane) of the glucose obtained was measured with FT-NMR DPX400, manufactured by Bruker Co. Its chemical shifts δ (ppm) were as follows:
α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

200 parts by weight of this glucose was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of lactic acid/phenyllactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 12 parts by weight of lactic acid and 10 parts by weight of phenyllactic acid was obtained.

The results of analysis of the lactic acid are shown below.
$^1$H-NMR (400 MHz, TMS, DMSO-$d_6$) δ/ppm: 1.25 (d, J=6.8 Hz, 3H), 4.07 (q, J=6.8 Hz, 1H).

The results of analysis of the phenyllactic acid are also shown below.
$^1$H-NMR (400 MHz, TMS, DMSO-$d_6$) δ/ppm: 2.82, 2.95, 4.16, 7.25.

The stereostructure of the lactic acid was also evaluated using an optically active column (RESTEK Column 13113, trade name; available from Uniflex Co.). As a result, it was ascertained that the lactic acid obtained was in the DL-form.

Meanwhile, the stereostructure of the phenyllactic acid was evaluated using an optically active column (RESTEK Column 13113, trade name; available from Uniflex Co.). As a result, it was ascertained that the phenyllactic acid obtained was in the L-form.

Using the reactor having a Dean-Stark trap, 12 parts by weight of the lactic acid, 10 parts by weight of the phenyllactic acid and 0.044 part by weight of tin dichloride were put into it and 220 parts by weight of mesitylene was added thereto to effect azeotropic dehydration in an atmosphere of nitrogen, and the water having gathered in the Dean-Stark trap was appropriately removed. The polymerization time was 40 hours, and the polyester copolymer obtained had a weight-average molecular weight of 150,000.

The polyester copolymer thus obtained, having a weight-average molecular weight of 150,000, was dissolved in chloroform. From the solution obtained, a film was formed by casting. The formed film was colorless and had the following physical properties.
Thickness: 40 to 41 μm
Tensile strength: 63 MPa (yield), 61 MPa (breaking)
Elongation: 7%

EXAMPLE 28

Using lactic acid and phenyllactic acid obtained through the same procedure as in Example 27, a polyester copolymer was synthesized. Using the reactor having a Dean-Stark trap, 12 parts by weight of the lactic acid, 10 parts by weight of the phenyllactic acid and 0.04 part by weight of zinc powder were put into it and 200 parts by weight of 1,3-dichlorobenzene was added thereto to effect azeotropic dehydration in an atmosphere of nitrogen, and the water having gathered in the Dean-Stark trap was appropriately removed. The polymerization time was 38 hours, and the polyester copolymer obtained had a weight-average molecular weight of 100,000.

The polyester copolymer thus obtained, having a weight-average molecular weight of 100,000, was dissolved in chloroform. From the solution obtained, a film was formed by casting. The formed film was colorless and had the following physical properties.
Thickness: 39 to 40 μm
Tensile strength: 51 MPa (yield), 49 MPa (breaking)
Elongation: 6%

EXAMPLE 29

Reclaimed paper for PPC (EN-500, A4, available from CANON SALES CO., INC.) having been used (a copy had been taken on one side using a copying machine) was cut in a size of 5 mm square, and 500 parts by weight of the same was introduced into 15,050 parts by weight of an enzyme solution, followed by stirring at 45° C. for 10 hours. As the enzyme solution, used was a solution prepared by dissolving 50 parts by weight of cellulase (MEISELASE TP60, trade name; available from Meiji Seika Kaisha, Ltd.) in 15,000 parts by weight of an aqueous acetic acid/sodium acetate solution (pH 4.5). After the reaction was completed, 1,000 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 280 parts by weight of glucose.

280 parts by weight of this glucose was mixed with 15,400 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 154 parts by weight of a pre-culture fluid of lactic acid/phenyllactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 18 parts by weight of lactic acid and 4 parts by weight of phenyllactic acid was obtained.

Using the reactor having a Dean-Stark trap, 18 parts by weight of the lactic acid, 4 parts by weight of the phenyllactic acid and 0.04 part by weight of tin oxide were put into it and 210 parts by weight of bromobenzene was added thereto to effect azeotropic dehydration in an atmosphere of nitrogen, and the water having gathered in the Dean-Stark trap was appropriately removed. The polymerization time was 45 hours, and the polyester copolymer obtained had a weight-average molecular weight of 200,000.

The polyester copolymer thus obtained, having a weight-average molecular weight of 200,000, was dissolved in chloroform. From the solution obtained, a film was formed by casting. The formed film was colorless and had the following physical properties.
Thickness: 39 to 40 μm
Tensile strength: 67 MPa (yield), 66 MPa (breaking)
Elongation: 11%

EXAMPLE 30

Using lactic acid and phenyllactic acid obtained through the same procedure as in Example 29, a polyester copolymer was synthesized. Using the reactor having a Dean-Stark trap, 18 parts by weight of the lactic acid, 4 parts by weight of the phenyllactic acid and 0.036 part by weight of p-toluenesulfonic acid were put into it and 200 parts by weight of 1,2-dichlorobenzene was added thereto to effect azeotropic dehydration, and the water having gathered in the Dean-Stark trap was appropriately removed. The polymerization time was 30 hours, and the polyester copolymer obtained had a weight-average molecular weight of 40,000.

The polyester copolymer thus obtained, having a weight-average molecular weight of 40,000, was dissolved in chloroform. From the solution obtained, a film was formed by casting. The formed film was colorless and had the following physical properties.
Thickness: 39 to 40 μm
Tensile strength: 20 MPa (yield), 19 MPa (breaking)
Elongation: 2%

EXAMPLE 31

370 parts by weight of starch (available from Wako Pure Chemical Industries, Ltd.) was introduced into 3,300 parts by weight of water and was dissolved therein with heating. To the aqueous solution formed, 3,700 parts by weight of 3 mol/l sulfuric acid was added, followed by stirring at 80° C. for 5 hours to carry out reaction. After the reaction was completed, anhydrous sodium carbonate was added to neutralize the aqueous solution, which was then further passed through an ion-exchange column (AMBERLITE IR-120B, trade name; available from Orugano K.K.), and the solvent was evaporated off. Then, the resultant reaction mixture was separated and purified to obtain 220 parts by weight of glucose.

The $^{13}C$-NMR (100 MHz, TMS, DMSO-$d_6$) of the glucose obtained was measured with FT-NMR DPX400, manufactured by Bruker Co. Its chemical shifts δ (ppm) were as follows:
α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

220 parts by weight of this glucose was mixed with 12,100 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 121 parts by weight of a pre-culture fluid of 2-hydroxyisocaproic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure. Thereafter, the solid content having remained was heated under reduced pressure. The gas having sublimated was cooled and the solid matter having precipitated was collected to obtain 10 parts by weight of 2-hydroxyisocaproic acid.

The $^{13}$C-NMR (100 MHz, TMS, CDCl$_3$) of the 2-hydroxyisocaproic acid thus obtained was measured to obtain the results as follows: (δ/ppm); 180.25, 68.95, 43.16, 24.45, 23.20, 21.42. Thus, it was ascertained that the desired 2-hydroxyisocaproic acid was obtained.

Its stereostructure was also evaluated using an optically active column (CYCLODEX-B, trade name; available from J & W Scientific Co.). As a result, it was ascertained that the 2-hydroxyisocaproic acid obtained was in the L-form.

Using a reactor having a Dean-Stark trap, 10 parts by weight of the 2-hydroxyisocaproic acid and 0.02 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 40 hours, and the aliphatic polyester obtained had a weight-average molecular weight of 90,000.

Its $^{13}$C-NMR (100 MHz, TMS, CDCl$_3$) was also measured to obtain the results (δ/ppm) of 169.78, 71.38, 39.33, 24.53, 23.00, 21.43. Thus, it was ascertained that the desired aliphatic polyester was synthesized.

The aliphatic polyester thus obtained, having a weight-average molecular weight of 90,000, was dissolved in chloroform. From the solution obtained, a film was formed by casting. The formed film was colorless and had the following physical properties.
Thickness: 38 to 39 μm
Tensile strength: 48 MPa (yield), 48 MPa (breaking)
Elongation: 5%

EXAMPLE 32

Using 2-hydroxyisocaproic acid obtained through the same procedure as in Example 31, an aliphatic polyester was synthesized. Using the reactor having a Dean-Stark trap, 10 parts by weight of the 2-hydroxyisocaproic acid and 0.02 part by weight of zinc chloride were put into it and 100 parts by weight of 1,3-dichlorobenzene was added thereto to effect azeotropic dehydration in an atmosphere of nitrogen, and the water having gathered in the Dean-Stark trap was appropriately removed. The polymerization time was 45 hours, and the aliphatic polyester obtained had a weight-average molecular weight of 140,000.

The aliphatic polyester thus obtained, having a weight-average molecular weight of 140,000, was dissolved in chloroform. From the solution obtained, a film was formed by casting. The formed film was colorless and had the following physical properties.
Thickness: 39 to 40 μm
Tensile strength: 57 MPa (yield), 56 MPa (breaking)
Elongation: 9%

EXAMPLE 33

Using 2-hydroxyisocaproic acid obtained through the same procedure as in Example 31, an aliphatic polyester was synthesized. Using the reactor having a Dean-Stark trap, 9 parts by weight of the 2-hydroxyisocaproic acid and 0.018 part by weight of tin octylate were put into it and 90 parts by weight of mesitylene was added thereto to effect azeotropic dehydration in an atmosphere of nitrogen, and the water having gathered in the Dean-Stark trap was appropriately removed. The polymerization time was 40 hours, and the aliphatic polyester obtained had a weight-average molecular weight of 50,000.

Its $^{13}$C-NMR was also measured to find that the same spectrum as that in Example 31 was obtained, and it was ascertained that the desired aliphatic polyester was obtained.

The aliphatic polyester thus obtained, having a weight-average molecular weight of 50,000, was dissolved in chloroform. From the solution obtained, a film was formed by casting. The formed film was colorless and had the following physical properties.
Thickness: 38 to 39 μm
Tensile strength: 20 MPa (yield), 20 MPa (breaking)
Elongation: 3%

EXAMPLE 34

Using 2-hydroxyisocaproic acid obtained through the same procedure as in Example 31, an aliphatic polyester was synthesized. Using the reactor having a Dean-Stark trap, 9 parts by weight of the 2-hydroxyisocaproic acid and 0.02 part by weight of tin powder were put into it and 100 parts by weight of diphenyl ether was added thereto to effect azeotropic dehydration at 130° C./12 mmHg, and the water having gathered in the Dean-Stark trap was appropriately removed. The polymerization time was 48 hours, and the aliphatic polyester obtained had a weight-average molecular weight of 190,000.

The aliphatic polyester thus obtained, having a weight-average molecular weight of 190,000, was dissolved in chloroform. From the solution obtained, a film was formed by casting. The formed film was colorless and had the following physical properties.
Thickness: 39 to 40 μm
Tensile strength: 69 MPa (yield), 67 MPa (breaking)
Elongation: 13%

EXAMPLE 35

370 parts by weight of starch (available from Wako Pure Chemical Industries, Ltd.) was introduced into 3,300 parts by weight of water and was dissolved therein with heating. To the aqueous solution formed, 3,700 parts by weight of 3 mol/l sulfuric acid was added, followed by stirring at 80° C. for 5 hours to carry out reaction. After the reaction was completed, anhydrous sodium carbonate was added to neutralize the aqueous solution, which was then further passed through an ion-exchange column (AMBERLITE IR-120B, trade name; available from Orugano K.K.), and the solvent was evaporated off. Then, the resultant reaction mixture was separated and purified to obtain 220 parts by weight of glucose.

The $^{13}$C-NMR (100 MHz, TMS, DMSO-d$_6$) of the glucose obtained was measured with FT-NMR DPX400, manufactured by Bruker Co. Its chemical shifts δ (ppm) were as follows:

α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

220 parts by weight of this glucose was mixed with 12,100 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 121 parts by weight of a pre-culture fluid of 2-hydroxyisocaproic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure. Thereafter, the solid content having remained was heated under reduced pressure. The gas having sublimated was cooled and the solid matter having precipitated was collected to obtain 10 parts by weight of 2-hydroxyisocaproic acid.

The $^{13}$C-NMR (100 MHz, CDCl$_3$) of this 2-hydroxyisocaproic acid was measured to obtain the results (δ/ppm) of 180.25, 68.95, 43.16, 24.45, 23.20, 21.42. Thus, it was ascertained that the desired 2-hydroxyisocaproic acid was obtained.

Using the reactor having a Dean-Stark trap, 10 parts by weight of the 2-hydroxyisocaproic acid and 0.2 part by weight of p-toluenesulfonic acid were put into it and 600 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The residue formed was recrystallized from ether to obtain 8.2 parts by weight of a cyclic dimer lactide.

The $^{13}$C-NMR (100 MHz, TMS, CDCl$_3$) of the cyclic dimer lactide obtained was measured to obtain the results (δ/ppm) of 167.33, 74.14, 38.87, 23.89, 23.03, 21.33. Thus, it was ascertained that the desired cyclic dimer lactide was obtained.

8.2 parts by weight of the cyclic dimer lactide and 0.01 part by weight of tin chloride were heated at 150° C. for 12 hours in an atmosphere of nitrogen to effect ring-opening polymerization. The aliphatic polyester thus obtained had a weight-average molecular weight of 180,000.

The $^{13}$C-NMR (100 MHz, TMS, CDCl$_3$) of this aliphatic polyester was measured to obtain the results (δ/ppm) of 169.78, 71.38, 39.33, 24.53, 23.00, 21.43. Thus, it was ascertained that the desired aliphatic polyester was synthesized.

The aliphatic polyester thus obtained, having a weight-average molecular weight of 180,000, was dissolved in chloroform. From the solution obtained, a film was formed by casting. The formed film was colorless and had the following physical properties.

Thickness: 38 to 39 μm
Tensile strength: 68 MPa (yield), 68 MPa (breaking)
Elongation: 13%

EXAMPLE 36

Using a cyclic dimer lactide obtained through the same procedure as in Example 35, an aliphatic polyester was synthesized. That is, 8.2 parts by weight of the cyclic dimer lactide and 0.01 part by weight of zinc chloride were heated at 120° C. for 5 hours in an atmosphere of nitrogen to effect ring-opening polymerization. The aliphatic polyester thus obtained had a weight-average molecular weight of 50,000. Its $^{13}$C-NMR was measured to find that the same spectrum as that in Example 35 was obtained, and it was ascertained that the desired aliphatic polyester was obtained.

The aliphatic polyester thus obtained, having a weight-average molecular weight of 50,000, was dissolved in chloroform. From the solution obtained, a film was formed by casting. The formed film was colorless and had the following physical properties.

Thickness: 39 to 40 μm
Tensile strength: 29 MPa (yield), 29 MPa (breaking)
Elongation: 4%

EXAMPLE 37

Using a cyclic dimer lactide obtained through the same procedure as in Example 35, an aliphatic polyester was synthesized. That is, 7.4 parts by weight of the cyclic dimer lactide and 0.008 part by weight of tin octylate were heated at 180° C. for 30 hours in an atmosphere of nitrogen to effect ring-opening polymerization. The aliphatic polyester thus obtained had a weight-average molecular weight of 680,000. Its $^{13}$C-NMR was measured to find that the same spectrum as that in Example 35 was obtained, and it was ascertained that the desired aliphatic polyester was obtained.

The aliphatic polyester thus obtained, having a weight-average molecular weight of 680,000, was dissolved in chloroform. From the solution obtained, a film was formed by casting. The formed film was colorless and had the following physical properties.

Thickness: 38 to 39 μm
Tensile strength: 98 MPa (yield), 98 MPa (breaking)
Elongation: 30%

EXAMPLE 38

Using a cyclic dimer lactide obtained through the same procedure as in Example 35, an aliphatic polyester was synthesized. That is, 7.4 parts by weight of the cyclic dimer lactide and 0.007 part by weight of tin powder were heated at 160° C. for 18 hours in an atmosphere of nitrogen to effect ring-opening polymerization. The aliphatic polyester thus obtained had a weight-average molecular weight of 390,000. Its $^{13}$C-NMR was measured to find that the same spectrum as that in Example 35 was obtained, and it was ascertained that the desired aliphatic polyester was obtained.

The aliphatic polyester thus obtained, having a weight-average molecular weight of 390,000, was dissolved in chloroform. From the solution obtained, a film was formed by casting. The formed film was colorless and had the following physical properties.

Thickness: 39 to 40 μm
Tensile strength: 88 MPa (yield), 87 MPa (breaking)
Elongation: 22%

EXAMPLE 39

370 parts by weight of starch (available from Wako Pure Chemical Industries, Ltd.) was introduced into 3,300 parts by weight of water and was dissolved therein with heating. To the aqueous solution formed, 3,700 parts by weight of 3 mol/l sulfuric acid was added, followed by stirring at 80° C. for 5 hours to carry out reaction. After the reaction was completed, anhydrous sodium carbonate was added to neutralize the aqueous solution, which was then further passed through an ion-exchange column (AMBERLITE IR-120B, trade name; available from Orugano K.K.), and the solvent was evaporated off. Then, the resultant reaction mixture was separated and purified to obtain 220 parts by weight of glucose.

The $^{13}$C-NMR (100 MHz, TMS, DMSO-$d_6$) of the glucose obtained was measured with FT-NMR DPX400, manufactured by Bruker Co. Its chemical shifts δ (ppm) were as follows:
α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

220 parts by weight of this glucose was mixed with 12,100 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 121 parts by weight of a pre-culture fluid of phenyllactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by purification to obtain 10 parts by weight of phenyllactic acid.

The $^{13}$C-NMR (100 MHz, TMS, CDCl$_3$) of the phenyllactic acid thus obtained was measured to obtain the results (δ/ppm) of 177.92, 137.63, 130.30, 129.46, 127.82, 72.05, 40.38, and it was ascertained that the desired phenyllactic acid was obtained.

Using the reactor having a Dean-Stark trap, 10 parts by weight of the phenyllactic acid and 0.2 part by weight of p-toluenesulfonic acid were put into it and 600 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The residue formed was recrystallized from ether to obtain 8.7 parts by weight of a cyclic dimer lactide.

8.7 parts by weight of the cyclic dimer lactide and 0.01 part by weight of tin chloride were heated at 160° C. for 10 hours in an atmosphere of nitrogen to effect ring-opening polymerization. The aromatic polyester thus obtained had a weight-average molecular weight of 190,000.

The aromatic polyester thus obtained, having a weight-average molecular weight of 190,000, was dissolved in chloroform. From the solution obtained, a film was formed by casting. The formed film was colorless and had the following physical properties.
Thickness: 39 to 40 μm
Tensile strength: 69 MPa (yield), 69 MPa (breaking)
Elongation: 12%

EXAMPLE 40

Using a cyclic dimer lactide obtained through the same procedure as in Example 39, an aromatic polyester was synthesized. That is, 8.7 parts by weight of the cyclic dimer lactide and 0.01 part by weight of zinc chloride were heated at 120° C. for 5 hours in an atmosphere of nitrogen to effect ring-opening polymerization. The aromatic polyester thus obtained had a weight-average molecular weight of 50,000.

The aromatic polyester thus obtained, having a weight-average molecular weight of 50,000, was dissolved in chloroform. From the solution obtained, a film was formed by casting. The formed film was colorless and had the following physical properties.
Thickness: 40 to 41 μm
Tensile strength: 31 MPa (yield), 30 MPa (breaking)
Elongation: 3%

EXAMPLE 41

Using a cyclic dimer lactide obtained through the same procedure as in Example 39, an aromatic polyester was synthesized. That is, 7.8 parts by weight of the cyclic dimer lactide and 0.007 part by weight of tin octylate were heated at 180° C. for 33 hours in an atmosphere of nitrogen to effect ring-opening polymerization. The aromatic polyester thus obtained had a weight-average molecular weight of 700,000.

The aromatic polyester thus obtained, having a weight-average molecular weight of 700,000, was dissolved in chloroform. From the solution obtained, a film was formed by casting. The formed film was colorless and had the following physical properties.
Thickness: 39 to 40 μm
Tensile strength: 98 MPa (yield), 98 MPa (breaking)
Elongation: 25%

EXAMPLE 42

Using a cyclic dimer lactide obtained through the same procedure as in Example 39, an aromatic polyester was synthesized. That is, 7.8 parts by weight of the cyclic dimer lactide and 0.006 part by weight of tin powder were heated at 160° C. for 18 hours in an atmosphere of nitrogen to effect ring-opening polymerization. The aromatic polyester thus obtained had a weight-average molecular weight of 380,000.

The aromatic polyester thus obtained, having a weight-average molecular weight of 380,000, was dissolved in chloroform. From the solution obtained, a film was formed by casting. The formed film was colorless and had the following physical properties.
Thickness: 38 to 39 μm
Tensile strength: 87 MPa (yield), 86 MPa (breaking)
Elongation: 16%

EXAMPLE 43

340 parts by weight of starch (available from Wako Pure Chemical Industries, Ltd.) was introduced into 3,000 parts by weight of water and was dissolved therein with heating. To the aqueous solution formed, 3,400 parts by weight of 3 mol/l sulfuric acid was added, followed by stirring at 80° C.

for 5 hours to carry out reaction. After the reaction was completed, anhydrous sodium carbonate was added to neutralize the aqueous solution, which was then further passed through an ion-exchange column (AMBERLITE IR-120B, trade name; available from Orugano K.K.), and the solvent was evaporated off. Then, the resultant reaction mixture was separated and purified to obtain 200 parts by weight of glucose.

The $^{13}$C-NMR (100 MHz, TMS, DMSO-$d_6$) of the glucose obtained was measured with FT-NMR DPX400, manufactured by Bruker Co. Its chemical shifts δ (ppm) were as follows:

α-Type: 92.12, 73.04, 72.29, 71.80, 70.58, 61.20;
β-Type: 96.79, 76.70, 76.59, 74.78, 70.30, 61.00.

From the above results of the measurements, it was ascertained that the desired glucose was obtained.

200 parts by weight of this glucose was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of 2-hydroxyisocaproic acid/lactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 10 parts by weight of 2-hydroxyisocaproic acid and 12 parts by weight of lactic acid was obtained.

Its $^1$H-NMR (400 MHz, TMS, DMSO-$d_6$) was measured to obtain the results (δ/ppm) as follows:
2-hydroxyisocaproic acid: 0.88 (t, 6H), 1.37 to 1.48 (m, 2H), 1.72 to 1.82 (m, 1H), 3.94 (dd, 1H);
lactic acid: 1.25 (d, J=6.8 Hz, 3H), 4.07 (q, J=6.8 Hz, 1H).

Its $^{13}$C-NMR (100 MHz, TMS, DMSO-$d_6$) was also measured to obtain the results (δ/ppm) as follows:
2-hydroxyisocaproic acid: 21.43, 23.12, 23.84, 42.84, 68.07, 176.23;
lactic acid: 20.39, 65.82, 176.42.

The stereostructure of the 2-hydroxyisocaproic acid was also evaluated using an optically active column (CYCLO-DEX-B, trade name; available from J & W Scientific Co.). As a result, it was ascertained that the 2-hydroxyisocaproic acid obtained was in the L-form.

Meanwhile, the stereostructure of the lactic acid was evaluated using an optically active column (RESTEK Column 13113, trade name; available from Uniflex Co.). As a result, it was ascertained that the lactic acid obtained was in the DL-form.

Using the reactor having a Dean-Stark trap, 10 parts by weight of the 2-hydroxyisocaproic acid, 12 parts by weight of the lactic acid and 0.044 part by weight of tin dichloride were put into it and 220 parts by weight of mesitylene was added thereto to effect azeotropic dehydration in an atmosphere of nitrogen, and the water having gathered in the Dean-Stark trap was appropriately removed. The polymerization time was 40 hours, and the polyester copolymer obtained had a weight-average molecular weight of 170,000.

Its $^{13}$C-NMR (100 MHz, TMS, CDCl$_3$) was measured to obtain the results (δ/ppm) of 16.66, 21.43, 22.99, 24.55, 39.30, 68.97, 71.37, 169.51, 169.76. Thus, it was ascertained that the desired aliphatic polyester copolymer was synthesized.

The aliphatic polyester copolymer thus obtained, having a weight-average molecular weight of 170,000, was dissolved in chloroform. From the solution obtained, a film was formed by casting. The formed film was colorless and had the following physical properties.
Thickness: 38 to 39 μm
Tensile strength: 61 MPa (yield), 59 MPa (breaking)
Elongation: 14%

EXAMPLE 44

Using 2-hydroxyisocaproic acid and lactic acid obtained through the same procedure as in Example 43, an aliphatic polyester copolymer was synthesized. Using the reactor having a Dean-Stark trap, 10 parts by weight of the 2-hydroxyisocaproic acid, 12 parts by weight of the lactic acid and 0.04 part by weight of zinc powder were put into it and 200 parts by weight of 1,3-dichlorobenzene was added thereto to effect azeotropic dehydration in an atmosphere of nitrogen, and the water having gathered in the Dean-Stark trap was appropriately removed. The polymerization time was 38 hours, and the aliphatic polyester copolymer obtained had a weight-average molecular weight of 100,000.

Its $^{13}$C-NMR was also measured to find that the same spectrum as that in Example 43 was obtained, and it was ascertained that the desired aliphatic polyester copolymer was synthesized.

The aliphatic polyester copolymer thus obtained, having a weight-average molecular weight of 100,000, was dissolved in chloroform. From the solution obtained, a film was formed by casting. The formed film was colorless and had the following physical properties.
Thickness: 39 to 40 μm
Tensile strength: 49 MPa (yield), 49 MPa (breaking)
Elongation: 6%

EXAMPLE 45

200 parts by weight of glucose obtained through the same procedure as in Example 43 was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of 2-hydroxyisocaproic acid/lactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 9 parts by weight of 2-hydroxyisocaproic acid and 11 parts by weight of lactic acid was obtained.

Using the reactor having a Dean-Stark trap, 9 parts by weight of the 2-hydroxyisocaproic acid, 11 parts by weight of the lactic acid and 0.04 part by weight of tin octylate were put into it and 210 parts by weight of mesitylene was added thereto to effect azeotropic dehydration in an atmosphere of nitrogen, and the water having gathered in the Dean-Stark trap was appropriately removed. The polymerization time was 36 hours, and the aliphatic polyester copolymer obtained had a weight-average molecular weight of 60,000.

Its $^{13}$C-NMR was also measured to find that the same spectrum as that in Example 43 was obtained, and it was ascertained that the desired aliphatic polyester copolymer was synthesized.

The aliphatic polyester copolymer thus obtained, having a weight-average molecular weight of 60,000, was dissolved in chloroform. From the solution obtained, a film was formed by casting. The formed film was colorless and had the following physical properties.
Thickness: 38 to 39 μm
Tensile strength: 22 MPa (yield), 22 MPa (breaking)
Elongation: 3%

EXAMPLE 46

Using 2-hydroxyisocaproic acid and lactic acid obtained through the same procedure as in Example 45, an aliphatic polyester copolymer was synthesized. Using the reactor having a Dean-Stark trap, 9 parts by weight of the 2-hydroxyisocaproic acid, 11 parts by weight of the lactic acid and 0.036 part by weight of tin powder were put into it and 260 parts by weight of diphenyl ether was added thereto to effect azeotropic dehydration at 130° C./12 mmHg, and the water having gathered in the Dean-Stark trap was appropriately removed. The polymerization time was 48 hours, and the aliphatic polyester copolymer obtained had a weight-average molecular weight of 290,000.

Its $^{13}$C-NMR was also measured to find that the same spectrum as that in Example 43 was obtained, and it was ascertained that the desired aliphatic polyester copolymer was synthesized.

The aliphatic polyester copolymer thus obtained, having a weight-average molecular weight of 290,000, was dissolved in chloroform. From the solution obtained, a film was formed by casting. The formed film was colorless and had the following physical properties.
Thickness: 39 to 40 μm
Tensile strength: 74 MPa (yield), 73 MPa (breaking)
Elongation: 23%

EXAMPLE 47

200 parts by weight of glucose obtained through the same procedure as in Example 43 was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with a mixed gas of 98% of nitrogen and 2% of oxygen to bring the inside of the bottle into a slightly aerobic condition, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of 2-hydroxyisocaproic acid/lactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 4 parts by weight of 2-hydroxyisocaproic acid and 18 parts by weight of lactic acid was obtained.

Using the reactor having a Dean-Stark trap, 4 parts by weight of the 2-hydroxyisocaproic acid, 18 parts by weight of the lactic acid and 0.04 part by weight of tin oxide were put into it and 210 parts by weight of bromobenzene was added thereto to effect azeotropic dehydration in an atmosphere of nitrogen, and the water having gathered in the Dean-Stark trap was appropriately removed. The polymerization time was 45 hours, and the aliphatic polyester copolymer obtained had a weight-average molecular weight of 220,000.

Its $^{13}$C-NMR was also measured to find that the same spectrum as that in Example 43 was obtained, and it was ascertained that the desired aliphatic polyester copolymer was synthesized.

The aliphatic polyester copolymer thus obtained, having a weight-average molecular weight of 220,000, was dissolved in chloroform. From the solution obtained, a film was formed by casting. The formed film was colorless and had the following physical properties.
Thickness: 37 to 38 μm
Tensile strength: 69 MPa (yield), 67 MPa (breaking)
Elongation: 18%

EXAMPLE 48

Using 2-hydroxyisocaproic acid and lactic acid obtained through the same procedure as in Example 47, an aliphatic polyester copolymer was synthesized. Using the reactor having a Dean-Stark trap, 4 parts by weight of the 2-hydroxyisocaproic acid, 18 parts by weight of the lactic acid and 0.036 part by weight of p-toluenesulfonic acid were put into it and 200 parts by weight of 1,2-dichlorobenzene was added thereto to effect azeotropic dehydration in an atmosphere of nitrogen, and the water having gathered in the Dean-Stark trap was appropriately removed. The polymerization time was 30 hours, and the aliphatic polyester copolymer obtained had a weight-average molecular weight of 40,000.

Its $^{13}$C-NMR was also measured to find that the same spectrum as that in Example 43 was obtained, and it was ascertained that the desired aliphatic polyester copolymer was synthesized.

The aliphatic polyester copolymer thus obtained, having a weight-average molecular weight of 40,000, was dissolved in chloroform. From the solution obtained, a film was formed by casting. The formed film was colorless and had the following physical properties.
Thickness: 40 to 41 μm
Tensile strength: 20 MPa (yield), 20 MPa (breaking)
Elongation: 2%

The following Examples 49 to 74 concern the polyester production process comprising the step of obtaining the substituted α-hydroxy acid by the direct fermentation of starch with a microorganism, described in the second embodiment. As the microorganism, used is an isolated strain of *Clostridium beijerinckii* strain HICA432 (FERMP-18373), obtained upon studies of the ability to further produce the substituted α-hydroxy acid from starch with respect to the 2-hydroxyisocaproic acid productive strain, strain HICA432, used in Examples 1 to 48.

The strain HICA432 has been ascertained to be capable of producing not only the 2-hydroxyisocaproic acid, but also lactic acid and phenyllactic acid. Accordingly, in the following, the strain HICA432 is also called a 2-hydroxyisocaproic acid productive strain, a lactic acid productive strain, and a phenyllactic acid productive strain.

EXAMPLE 49

250 parts by weight of starch (available from Wako Pure Chemical Industries, Ltd.) was mixed with 12,100 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 121 parts by weight of a pre-culture fluid of 2-hydroxyisocaproic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure. Thereafter, the solid content having remained was heated under reduced pressure. The gas having sublimated was cooled and the solid matter having precipitated was collected to obtain 10 parts by weight of 2-hydroxyisocaproic acid.

The $^{13}$C-NMR (100 MHz, TMS, CDCl$_3$) of the 2-hydroxyisocaproic acid thus obtained was measured to obtain the results as follows: (δ/ppm); 180.25, 68.95, 43.16, 24.45, 23.20, 21.42. Thus, it was ascertained that the desired 2-hydroxyisocaproic acid was obtained.

Its stereostructure was also evaluated using an optically active column (CYCLODEX-B, trade name; available from J & W Scientific Co.). As a result, it was ascertained that the 2-hydroxyisocaproic acid obtained was in the L-form.

Next, using a reactor having a Dean-Stark trap, 10 parts by weight of the 2-hydroxyisocaproic acid and 0.02 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 40 hours, and the aliphatic polyester obtained had a weight-average molecular weight of 90,000.

Its $^{13}$C-NMR (100 MHz, TMS, CDCl$_3$) was also measured to obtain the results (δ/ppm) of 169.78, 71.38, 39.33, 24.53, 23.00, 21.43. Thus, it was ascertained that the desired aliphatic polyester was synthesized.

The aliphatic polyester thus obtained, having a weight-average molecular weight of 90,000, was dissolved in chloroform. From the solution obtained, a film was formed by casting. The formed film was colorless and had the following physical properties.
Thickness: 38 to 39 μm
Tensile strength: 48 MPa (yield), 48 MPa (breaking)
Elongation: 5%

EXAMPLE 50

Using 2-hydroxyisocaproic acid obtained through the same procedure as in Example 49, an aliphatic polyester was synthesized. Using the reactor having a Dean-Stark trap, 10 parts by weight of the 2-hydroxyisocaproic acid and 0.02 part by weight of zinc chloride were put into it and 100 parts by weight of 1,3-dichlorobenzene was added thereto to effect azeotropic dehydration in an atmosphere of nitrogen, and the water having gathered in the Dean-Stark trap was appropriately removed. The polymerization time was 45 hours, and the aliphatic polyester obtained had a weight-average molecular weight of 140,000.

The aliphatic polyester thus obtained, having a weight-average molecular weight of 140,000, was dissolved in chloroform. From the solution obtained, a film was formed by casting. The formed film was colorless and had the following physical properties.
Thickness: 39 to 40 μm
Tensile strength: 57 MPa (yield), 56 MPa (breaking)
Elongation: 9%

EXAMPLE 51

Using 2-hydroxyisocaproic acid obtained through the same procedure as in Example 49, an aliphatic polyester was synthesized. Using the reactor having a Dean-Stark trap, 9 parts by weight of the 2-hydroxyisocaproic acid and 0.018 part by weight of tin octylate were put into it and 90 parts by weight of mesitylene was added thereto to effect azeotropic dehydration in an atmosphere of nitrogen, and the water having gathered in the Dean-Stark trap was appropriately removed. The polymerization time was 40 hours, and the aliphatic polyester obtained had a weight-average molecular weight of 50,000.

Its $^{13}$C-NMR was also measured to find that the same spectrum as that in Example 49 was obtained, and it was ascertained that the desired aliphatic polyester was obtained.

The aliphatic polyester thus obtained, having a weight-average molecular weight of 50,000, was dissolved in chloroform. From the solution obtained, a film was formed by casting. The formed film was colorless and had the following physical properties.
Thickness: 38 to 39 μm
Tensile strength: 20 MPa (yield), 20 MPa (breaking)
Elongation: 3%

EXAMPLE 52

Using 2-hydroxyisocaproic acid obtained through the same procedure as in Example 49, an aliphatic polyester was synthesized. Using the reactor having a Dean-Stark trap, 9 parts by weight of the 2-hydroxyisocaproic acid and 0.02 part by weight of tin powder were put into it and 100 parts by weight of diphenyl ether was added thereto to effect azeotropic dehydration at 130° C./12 mmHg, and the water having gathered in the Dean-Stark trap was appropriately removed. The polymerization time was 48 hours, and the aliphatic polyester obtained had a weight-average molecular weight of 190,000.

The aliphatic polyester thus obtained, having a weight-average molecular weight of 190,000, was dissolved in chloroform. From the solution obtained, a film was formed by casting. The formed film was colorless and had the following physical properties.
Thickness: 39 to 40 μm
Tensile strength: 69 MPa (yield), 67 MPa (breaking)
Elongation: 13%

EXAMPLE 53

Using 2-hydroxyisocaproic acid obtained through the same procedure as in Example 49, it was converted into a cyclic dimer lactide in the following way.

Using the reactor having a Dean-Stark trap, 9 parts by weight of the 2-hydroxyisocaproic acid and 0.18 part by weight of p-toluenesulfonic acid were put into it and 540 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The residue formed was recrystallized from ether to obtain 7.4 parts by weight of a cyclic dimer lactide.

The $^{13}$C-NMR (100 MHz, TMS, CDCl$_3$) of the cyclic dimer lactide obtained was measured to obtain the results ($\delta$/ppm) of 167.33, 74.14, 38.87, 23.89, 23.03, 21.33. Thus, it was ascertained that the desired cyclic dimer lactide was obtained.

7.4 parts by weight of the cyclic dimer lactide and 0.01 part by weight of tin chloride were heated at 150° C. for 12 hours in an atmosphere of nitrogen to effect ring-opening polymerization. The aliphatic polyester thus obtained had a weight-average molecular weight of 180,000.

The $^{13}$C-NMR (100 MHz, TMS, CDCl$_3$) of this aliphatic polyester was measured to obtain the results ($\delta$/ppm) of 169.78, 71.38, 39.33, 24.53, 23.00, 21.43. Thus, it was ascertained that the desired aliphatic polyester was synthesized.

The aliphatic polyester thus obtained, having a weight-average molecular weight of 180,000, was dissolved in chloroform. From the solution obtained, a film was formed by casting. The formed film was colorless and had the following physical properties.
Thickness: 38 to 39 μm
Tensile strength: 68 MPa (yield), 68 MPa (breaking)
Elongation: 13%

EXAMPLE 54

Using a cyclic dimer lactide obtained through the same procedure as in Example 53, an aliphatic polyester was synthesized. That is, 7.4 parts by weight of the cyclic dimer lactide and 0.007 part by weight of zinc powder were heated at 160° C. for 18 hours in an atmosphere of nitrogen to effect ring-opening polymerization. The aliphatic polyester thus obtained had a weight-average molecular weight of 390,000. Its $^{13}$C-NMR was measured to find that the same spectrum as that in Example 53 was obtained, and it was ascertained that the desired aliphatic polyester was obtained.

The aliphatic polyester thus obtained, having a weight-average molecular weight of 390,000, was dissolved in chloroform. From the solution obtained, a film was formed by casting. The formed film was colorless and had the following physical properties.
Thickness: 39 to 40 μm
Tensile strength: 88 MPa (yield), 87 MPa (breaking)
Elongation: 22%

EXAMPLE 55

Using a cyclic dimer lactide obtained through the same procedure as in Example 53, an aliphatic polyester was synthesized. That is, 7.4 parts by weight of the cyclic dimer lactide and 0.008 part by weight of tin octylate were heated at 180° C. for 30 hours in an atmosphere of nitrogen to effect ring-opening polymerization. The aliphatic polyester thus obtained had a weight-average molecular weight of 680,000. Its $^{13}$C-NMR was measured to find that the same spectrum as that in Example 53 was obtained, and it was ascertained that the desired aliphatic polyester was obtained.

The aliphatic polyester thus obtained, having a weight-average molecular weight of 680,000, was dissolved in chloroform. From the solution obtained, a film was formed by casting. The formed film was colorless and had the following physical properties.
Thickness: 38 to 39 μm
Tensile strength: 98 MPa (yield), 98 MPa (breaking)
Elongation: 30%

EXAMPLE 56

250 parts by weight of starch (available from Wako Pure Chemical Industries, Ltd.) was mixed with 12,100 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 121 parts by weight of a pre-culture fluid of phenyllactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by purification to obtain 10 parts by weight of phenyllactic acid.

The $^{13}$C-NMR (100 MHz, TMS, CDCl$_3$) of the phenyllactic acid thus obtained was measured to obtain the results ($\delta$/ppm) of 177.92, 137.63, 130.30, 129.46, 127.82, 72.05, 40.38, and it was ascertained that the desired phenyllactic acid was obtained.

Its stereostructure was also evaluated using an optically active column (CYCLODEX-B, trade name; available from J & W Scientific Co.). As a result, it was ascertained that the phenyllactic acid obtained was in the L-form.

Using the reactor having a Dean-Stark trap, 10 parts by weight of the phenyllactic acid and 0.018 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 44 hours, and the aromatic polyester obtained had a weight-average molecular weight of 180,000.

The aliphatic polyester thus obtained, having a weight-average molecular weight of 180,000, was dissolved in chloroform. From the solution obtained, a film was formed by casting. The formed film was colorless and had the following physical properties.
Thickness: 38 to 39 μm
Tensile strength: 69 MPa (yield), 69 MPa (breaking)
Elongation: 12%

EXAMPLE 57

Using phenyllactic acid obtained through the same procedure as in Example 56, an aromatic polyester was synthesized. Using the reactor having a Dean-Stark trap, 10 parts by weight of the phenyllactic acid and 0.02 part by weight of zinc chloride were put into it and 100 parts by weight of 1,3-dichlorobenzene was added thereto to effect azeotropic dehydration in an atmosphere of nitrogen, and the water having gathered in the Dean-Stark trap was appropriately removed. The polymerization time was 16 hours, and the aromatic polyester obtained had a weight-average molecular weight of 30,000.

The aromatic polyester thus obtained, having a weight-average molecular weight of 30,000, was dissolved in chloroform. From the solution obtained, a film was formed by casting. The formed film was colorless and had the following physical properties.
Thickness: 39 to 40 μm
Tensile strength: 20 MPa (yield), 19 MPa (breaking)
Elongation: 2%

EXAMPLE 58

Using phenyllactic acid obtained through the same procedure as in Example 56, an aromatic polyester was synthesized. Using the reactor having a Dean-Stark trap, 9 parts by weight of the phenyllactic acid and 0.015 part by weight of tin oxide were put into it and 90 parts by weight of mesitylene was added thereto to effect azeotropic dehydration in an atmosphere of nitrogen, and the water having gathered in the Dean-Stark trap was appropriately removed. The polymerization time was 40 hours, and the aromatic polyester obtained had a weight-average molecular weight of 90,000.

The aromatic polyester thus obtained, having a weight-average molecular weight of 90,000, was dissolved in chloroform. From the solution obtained, a film was formed by casting. The formed film was colorless and had the following physical properties.
Thickness: 38 to 39 μm
Tensile strength: 49 MPa (yield), 49 MPa (breaking)
Elongation: 5%

EXAMPLE 59

Using phenyllactic acid obtained through the same procedure as in Example 56, an aromatic polyester was synthesized. Using the reactor having a Dean-Stark trap, 9 parts by weight of the phenyllactic acid and 0.015 part by weight of tin powder were put into it and 100 parts by weight of diphenyl ether was added thereto to effect azeotropic dehydration at 130° C./12 mmHg, and the water having gathered in the Dean-Stark trap was appropriately removed. The polymerization time was 48 hours, and the aromatic polyester obtained had a weight-average molecular weight of 250,000.

The aromatic polyester thus obtained, having a weight-average molecular weight of 250,000, was dissolved in chloroform. From the solution obtained, a film was formed by casting. The formed film was colorless and had the following physical properties.
Thickness: 39 to 40 μm
Tensile strength: 82 MPa (yield), 81 MPa (breaking)
Elongation: 18%

EXAMPLE 60

Using phenyllactic acid obtained through the same procedure as in Example 56, it was converted into a cyclic dimer lactide in the following way.

Using the reactor having a Dean-Stark trap, 9 parts by weight of the phenyllactic acid and 0.18 part by weight of p-toluenesulfonic acid were put into it and 540 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The residue formed was recrystallized from ether to obtain 7.8 parts by weight of a cyclic dimer lactide.

7.8 parts by weight of the cyclic dimer lactide and 0.01 part by weight of tin chloride were heated at 160° C. for 10 hours in an atmosphere of nitrogen to effect ring-opening polymerization. The aromatic polyester thus obtained had a weight-average molecular weight of 190,000.

The aromatic polyester thus obtained, having a weight-average molecular weight of 190,000, was dissolved in chloroform. From the solution obtained, a film was formed by casting. The formed film was colorless and had the following physical properties.
Thickness: 39 to 40 μm
Tensile strength: 69 MPa (yield), 69 MPa (breaking)
Elongation: 12%

EXAMPLE 61

Using a cyclic dimer lactide obtained through the same procedure as in Example 60, an aromatic polyester was synthesized. That is, 7.8 parts by weight of the cyclic dimer lactide and 0.006 part by weight of tin powder were heated at 160° C. for 18 hours in an atmosphere of nitrogen to effect ring-opening polymerization. The aromatic polyester thus obtained had a weight-average molecular weight of 380,000.

The aromatic polyester thus obtained, having a weight-average molecular weight of 380,000, was dissolved in chloroform. From the solution obtained, a film was formed by casting. The formed film was colorless and had the following physical properties.
Thickness: 38 to 39 μm
Tensile strength: 87 MPa (yield), 86 MPa (breaking)
Elongation: 16%

EXAMPLE 62

Using a cyclic dimer lactide obtained through the same procedure as in Example 60, an aromatic polyester was synthesized. That is, 7.8 parts by weight of the cyclic dimer lactide and 0.007 part by weight of tin octylate were heated at 180° C. for 33 hours in an atmosphere of nitrogen to effect ring-opening polymerization. The aromatic polyester thus obtained had a weight-average molecular weight of 700,000.

The aromatic polyester thus obtained, having a weight-average molecular weight of 700,000, was dissolved in chloroform. From the solution obtained, a film was formed by casting. The formed film was colorless and had the following physical properties.
Thickness: 39 to 40 μm
Tensile strength: 98 MPa (yield), 98 MPa (breaking)
Elongation: 25%

EXAMPLE 63

400 parts by weight of starch (available from Wako Pure Chemical Industries, Ltd.) was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of 2-hydroxyisocaproic acid/lactic acid productive strain HICA432 isolated in the manner as described previously was added thereto by means of a syringe when the bottle was kept hermetically stoppered, followed by a static culture at 30° C. for 4 days. Thereafter, the culture fluid was filtered, and the water and volatile components of the filtrate obtained were evaporated off under normal-temperature reduced pressure, followed by NMR analysis. As a result, it was ascertained that a mixture of 10 parts by weight of 2-hydroxyisocaproic acid and 12 parts by weight of lactic acid was obtained.

Its $^1$H-NMR (400 MHz, TMS, DMSO-$d_6$) was measured to obtain the results (δ/ppm) as follows:

2-hydroxyisocaproic acid: 0.88 (t, 6H), 1.37 to 1.48 (m, 2H), 1.72 to 1.82 (m, 1H), 3.94 (dd, 1H);

lactic acid: 1.25 (d, J=6.8 Hz, 3H), 4.07 (q, J=6.8 Hz, 1H).

Its $^{13}$C-NMR (100 MHz, TMS, DMSO-$d_6$) was also measured to obtain the results (δ/ppm) as follows:

2-hydroxyisocaproic acid: 21.43, 23.12, 23.84, 42.84, 68.07, 176.23;

lactic acid: 20.39, 65.82, 176.42.

The stereostructure of the 2-hydroxyisocaproic acid was also evaluated using an optically active column (CYCLODEX-B, trade name; available from J & W Scientific Co.). As a result, it was ascertained that the 2-hydroxyisocaproic acid obtained was in the L-form.

Meanwhile, the stereostructure of the lactic acid was evaluated using an optically active column (RESTEK Column 13113, trade name; available from Uniflex Co.). As a result, it was ascertained that the lactic acid obtained was in the DL-form.

Using the reactor having a Dean-Stark trap, 10 parts by weight of the 2-hydroxyisocaproic acid, 12 parts by weight of the lactic acid and 0.044 part by weight of tin dichloride were put into it and 220 parts by weight of mesitylene was added thereto to effect azeotropic dehydration in an atmosphere of nitrogen, and the water having gathered in the Dean-Stark trap was appropriately removed. The polymerization time was 40 hours, and the aliphatic polyester copolymer obtained had a weight-average molecular weight of 170,000.

Its $^{13}$C-NMR (100 MHz, TMS, CDCl$_3$) was measured to obtain the results (δ/ppm) of 16.66, 21.43, 22.99, 24.55, 39.30, 68.97, 71.37, 169.51, 169.76. Thus, it was ascertained that the desired aliphatic polyester copolymer was synthesized.

The aliphatic polyester copolymer thus obtained, having a weight-average molecular weight of 170,000, was dissolved in chloroform. From the solution obtained, a film was formed by casting. The formed film was colorless and had the following physical properties.
Thickness: 38 to 39 μm
Tensile strength: 61 MPa (yield), 59 MPa (breaking)
Elongation: 14%

EXAMPLE 64

Using 2-hydroxyisocaproic acid and lactic acid obtained through the same procedure as in Example 63, an aliphatic polyester copolymer was synthesized. Using the reactor having a Dean-Stark trap, 10 parts by weight of the 2-hydroxyisocaproic acid, 12 parts by weight of the lactic acid and 0.04 part by weight of zinc powder were put into it and 200 parts by weight of 1,3-dichlorobenzene was added thereto to effect azeotropic dehydration in an atmosphere of nitrogen, and the water having gathered in the Dean-Stark trap was appropriately removed. The polymerization time was 38 hours, and the aliphatic polyester copolymer obtained had a weight-average molecular weight of 100,000.

Its $^{13}$C-NMR was also measured to find that the same spectrum as that in Example 63 was obtained, and it was ascertained that the desired aliphatic polyester copolymer was synthesized.

The aliphatic polyester copolymer thus obtained, having a weight-average molecular weight of 100,000, was dissolved in chloroform. From the solution obtained, a film was formed by casting. The formed film was colorless and had the following physical properties.
Thickness: 39 to 40 μm
Tensile strength: 49 MPa (yield), 49 MPa (breaking)
Elongation: 6%

EXAMPLE 65

Using 2-hydroxyisocaproic acid and lactic acid obtained through the same procedure as in Example 63, an aliphatic polyester copolymer was synthesized. Using the reactor having a Dean-Stark trap, 10 parts by weight of the 2-hydroxyisocaproic acid, 12 parts by weight of the lactic acid and 0.04 part by weight of tin octylate were put into it and 210 parts by weight of mesitylene was added thereto to effect azeotropic dehydration in an atmosphere of nitrogen, and the water having gathered in the Dean-Stark trap was appropriately removed. The polymerization time was 36 hours, and the aliphatic polyester copolymer obtained had a weight-average molecular weight of 60,000.

Its $^{13}$C-NMR was also measured to find that the same spectrum as that in Example 63 was obtained, and it was ascertained that the desired aliphatic polyester copolymer was synthesized.

The aliphatic polyester copolymer thus obtained, having a weight-average molecular weight of 60,000, was dissolved in chloroform. From the solution obtained, a film was formed by casting. The formed film was colorless and had the following physical properties.
Thickness: 38 to 39 μm
Tensile strength: 22 MPa (yield), 22 MPa (breaking)
Elongation: 3%

EXAMPLE 66

Using 2-hydroxyisocaproic acid and lactic acid obtained through the same procedure as in Example 63, an aliphatic polyester copolymer was synthesized. Using the reactor having a Dean-Stark trap, 10 parts by weight of the 2-hydroxyisocaproic acid, 12 parts by weight of the lactic acid and 0.036 part by weight of tin powder were put into it and 260 parts by weight of diphenyl ether was added thereto to effect azeotropic dehydration at 130° C./12 mmHg, and the water having gathered in the Dean-Stark trap was appropriately removed. The polymerization time was 48 hours, and the aliphatic polyester copolymer obtained had a weight-average molecular weight of 290,000.

Its $^{13}$C-NMR was also measured to find that the same spectrum as that in Example 63 was obtained, and it was ascertained that the desired aliphatic polyester copolymer was synthesized.

The aliphatic polyester copolymer thus obtained, having a weight-average molecular weight of 290,000, was dissolved in chloroform. From the solution obtained, a film was formed by casting. The formed film was colorless and had the following physical properties.
Thickness: 39 to 40 μm
Tensile strength: 74 MPa (yield), 73 MPa (breaking)
Elongation: 23%

EXAMPLE 67

400 parts by weight of starch (available from Wako Pure Chemical Industries, Ltd.) was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas to bring the inside of the bottle into a slightly aerobic state, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of 2-hydroxyisocaproic acid/ lactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 4 parts by weight of 2-hydroxyisocaproic acid and 18 parts by weight of lactic acid was obtained.

Using the reactor having a Dean-Stark trap, 4 parts by weight of the 2-hydroxyisocaproic acid, 18 parts by weight of the lactic acid and 0.04 part by weight of tin oxide were put into it and 210 parts by weight of bromobenzene was added thereto to effect azeotropic dehydration in an atmosphere of nitrogen, and the water having gathered in the Dean-Stark trap was appropriately removed. The polymerization time was 45 hours, and the aliphatic polyester copolymer obtained had a weight-average molecular weight of 220,000.

Its $^{13}$C-NMR was also measured to find that the same spectrum as that in Example 63 was obtained, and it was ascertained that the desired aliphatic polyester copolymer was synthesized.

The aliphatic polyester copolymer thus obtained, having a weight-average molecular weight of 220,000, was dissolved in chloroform. From the solution obtained, a film was formed by casting. The formed film was colorless and had the following physical properties.
Thickness: 37 to 38 μm
Tensile strength: 69 MPa (yield), 67 MPa (breaking)
Elongation: 18%

EXAMPLE 68

Using 2-hydroxyisocaproic acid and lactic acid obtained through the same procedure as in Example 67, an aliphatic polyester copolymer was synthesized. Using the reactor having a Dean-Stark trap, 4 parts by weight of the 2-hydroxyisocaproic acid, 18 parts by weight of the lactic acid and 0.036 part by weight of p-toluenesulfonic acid were put into it and 200 parts by weight of 1,2-dichlorobenzene was added thereto to effect azeotropic dehydration in an atmosphere of nitrogen, and the water having gathered in the Dean-Stark trap was appropriately removed. The polymerization time was 30 hours, and the aliphatic polyester copolymer obtained had a weight-average molecular weight of 40,000.

Its $^{13}$C-NMR was also measured to find that the same spectrum as that in Example 63 was obtained, and it was ascertained that the desired aliphatic polyester copolymer was synthesized.

The aliphatic polyester copolymer thus obtained, having a weight-average molecular weight of 40,000, was dissolved in chloroform. From the solution obtained, a film was formed by casting. The formed film was colorless and had the following physical properties.
Thickness: 40 to 41 μm
Tensile strength: 20 MPa (yield), 20 MPa (breaking)
Elongation: 2%

EXAMPLE 69

400 parts by weight of starch (available from Wako Pure Chemical Industries, Ltd.) was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of 2-hydroxyisocaproic acid/ phenyllactic acid productive strain HICA432 isolated in the manner as described previously was added thereto by means of a syringe when the bottle was kept hermetically stoppered, followed by a static culture at 30° C. for 6 days. Thereafter, the culture fluid was filtered, and the water and volatile components of the filtrate obtained were evaporated off under normal-temperature reduced pressure, followed by NMR analysis. As a result, it was ascertained that a mixture of 10 parts by weight of 2-hydroxyisocaproic acid and 12 parts by weight of phenyllactic acid was obtained.

Its $^1$H-NMR (400 MHz, TMS, DMSO-d$_6$) was measured to obtain the results (δ/ppm) as follows:
2-hydroxyisocaproic acid: 0.88 (t, 6H), 1.37 to 1.48 (m, 2H), 1.72 to 1.82 (m, 1H), 3.94 (dd, 1H);
phenyllactic acid: 2.82, 2.95, 4.16, 7.25.

The stereostructure of the 2-hydroxyisocaproic acid was also evaluated using an optically active column (CYCLO-DEX-B, trade name; available from J & W Scientific Co.). As a result, it was ascertained that the 2-hydroxyisocaproic acid obtained was in the L-form.

Meanwhile, the stereostructure of the lactic acid was evaluated using an optically active column (RESTEK Column 13113, trade name; available from Uniflex Co.). As a result, it was ascertained that the phenyllactic acid obtained was in the L-form.

Using the reactor having a Dean-Stark trap, 10 parts by weight of the 2-hydroxyisocaproic acid, 12 parts by weight of the phenyllactic acid and 0.044 part by weight of tin dichloride were put into it and 220 parts by weight of mesitylene was added thereto to effect azeotropic dehydration in an atmosphere of nitrogen, and the water having gathered in the Dean-Stark trap was appropriately removed. The polymerization time was 40 hours, and the polyester copolymer obtained had a weight-average molecular weight of 160,000.

The polyester copolymer thus obtained, having a weight-average molecular weight of 160,000, was dissolved in chloroform. From the solution obtained, a film was formed by casting. The formed film was colorless and had the following physical properties.
Thickness: 37 to 38 μm
Tensile strength: 60 MPa (yield), 60 MPa (breaking)
Elongation: 13%

EXAMPLE 70

Using 2-hydroxyisocaproic acid and phenyllactic acid obtained through the same procedure as in Example 69, a polyester copolymer was synthesized. Using the reactor having a Dean-Stark trap, 10 parts by weight of the 2-hydroxyisocaproic acid, 12 parts by weight of the phenyllactic acid and 0.04 part by weight of zinc powder were put into it and 200 parts by weight of 1,3-dichlorobenzene was added thereto to effect azeotropic dehydration in an atmosphere of nitrogen, and the water having gathered in the Dean-Stark trap was appropriately removed. The polymerization time was 38 hours, and the polyester copolymer obtained had a weight-average molecular weight of 110,000.

The polyester copolymer thus obtained, having a weight-average molecular weight of 110,000, was dissolved in chloroform. From the solution obtained, a film was formed by casting. The formed film was colorless and had the following physical properties.
Thickness: 39 to 40 μm
Tensile strength: 50 MPa (yield), 49 MPa (breaking)
Elongation: 7%

EXAMPLE 71

400 parts by weight of starch (available from Wako Pure Chemical Industries, Ltd.) was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of lactic acid/phenyllactic acid productive strain HICA432 isolated in the manner as described previously was added thereto by means of a syringe when the bottle was kept hermetically stoppered, followed by a static culture at 30° C. for 4 days. Thereafter, the culture fluid was filtered, and the water and volatile components of the filtrate obtained were evaporated off under normal-temperature reduced pressure, followed by NMR analysis. As a result, it was ascertained that a mixture of 12 parts by weight of lactic acid and 10 parts by weight of phenyllactic acid was obtained.

The results of analysis of the lactic acid are as follows:
$^1$H-NMR (400 MHz, TMS, DMSO-$d_6$) δ/ppm: 1.25 (d, J=6.8 Hz, 3H), 4.07 (q, J=6.8 Hz, 1H).

The results of analysis of the phenyllactic acid are also as follows:
$^1$H-NMR (400 MHz, TMS, DMSO-$d_6$) δ/ppm: 2.82, 2.95, 4.16, 7.25.

The stereostructure of the lactic acid was also evaluated using an optically active column (RESTEK Column 13113, trade name; available from Uniflex Co.). As a result, it was ascertained that the lactic acid obtained was in the DL-form.

Meanwhile, the stereostructure of the phenyllactic acid was evaluated using an optically active column (RESTEK Column 13113, trade name; available from Uniflex Co.). As a result, it was ascertained that the phenyllactic acid obtained was in the L-form.

Using the reactor having a Dean-Stark trap, 12 parts by weight of the lactic acid, 10 parts by weight of the phenyllactic acid and 0.044 part by weight of tin dichloride were put into it and 220 parts by weight of mesitylene was added thereto to effect azeotropic dehydration in an atmosphere of nitrogen, and the water having gathered in the Dean-Stark trap was appropriately removed. The polymerization time was 40 hours, and the polyester copolymer obtained had a weight-average molecular weight of 130,000.

The polyester copolymer thus obtained, having a weight-average molecular weight of 130,000, was dissolved in chloroform. From the solution obtained, a film was formed by casting. The formed film was colorless and had the following physical properties.
Thickness: 38 to 39 μm
Tensile strength: 61 MPa (yield), 60 MPa (breaking)
Elongation: 6%

EXAMPLE 72

Using lactic acid and phenyllactic acid obtained through the same procedure as in Example 71, a polyester copolymer was synthesized. Using the reactor having a Dean-Stark trap, 12 parts by weight of the lactic acid, 10 parts by weight of the phenyllactic acid and 0.04 part by weight of zinc powder were put into it and 200 parts by weight of 1,3-dichlorobenzene was added thereto to effect azeotropic dehydration in an atmosphere of nitrogen, and the water having gathered in the Dean-Stark trap was appropriately removed. The polymerization time was 38 hours, and the polyester copolymer obtained had a weight-average molecular weight of 80,000.

The polyester copolymer thus obtained, having a weight-average molecular weight of 80,000, was dissolved in chloroform. From the solution obtained, a film was formed by casting. The formed film was colorless and had the following physical properties.
Thickness: 39 to 40 μm
Tensile strength: 49 MPa (yield), 49 MPa (breaking)
Elongation: 6%

EXAMPLE 73

400 parts by weight of starch (available from Wako Pure Chemical Industries, Ltd.) was mixed with 11,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 110 parts by weight of a pre-culture fluid of lactic acid/phenyllactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 18 parts by weight of lactic acid and 4 parts by weight of phenyllactic acid was obtained.

Using the reactor having a Dean-Stark trap, 18 parts by weight of the lactic acid, 4 parts by weight of the phenyllactic acid and 0.04 part by weight of tin oxide were put into it and 210 parts by weight of bromobenzene was added thereto to effect azeotropic dehydration in an atmosphere of nitrogen, and the water having gathered in the Dean-Stark trap was appropriately removed. The polymerization time was 45 hours, and the polyester copolymer obtained had a weight-average molecular weight of 180,000.

The polyester copolymer thus obtained, having a weight-average molecular weight of 180,000, was dissolved in chloroform. From the solution obtained, a film was formed by casting. The formed film was colorless and had the following physical properties.
Thickness: 39 to 40 µm
Tensile strength: 67 MPa (yield), 64 MPa (breaking)
Elongation: 10%

EXAMPLE 74

Using lactic acid and phenyllactic acid obtained through the same procedure as in Example 73, a polyester copolymer was synthesized. Using the reactor having a Dean-Stark trap, 18 parts by weight of the lactic acid, 4 parts by weight of the phenyllactic acid and 0.036 part by weight of p-toluenesulfonic acid were put into it and 200 parts by weight of 1,2-dichlorobenzene was added thereto to effect azeotropic dehydration, and the water having gathered in the Dean-Stark trap was appropriately removed. The polymerization time was 30 hours, and the polyester copolymer obtained had a weight-average molecular weight of 30,000.

The polyester copolymer thus obtained, having a weight-average molecular weight of 30,000, was dissolved in chloroform. From the solution obtained, a film was formed by casting. The formed film was colorless and had the following physical properties.
Thickness: 39 to 40 µm
Tensile strength: 19 MPa (yield), 19 MPa (breaking)
Elongation: 2%

The following Examples 75 to 82 concern the polyester production process comprising the step of obtaining the substituted α-hydroxy acid by the fermentation of xylose with a microorganism, which is described in the third embodiment.

As the microorganism, used is an isolated strain of *Clostridium beijerinckii* strain HICA432 (FERMP-18373), obtained upon studies of the ability to further produce the substituted α-hydroxy acid from xylose with respect to the 2-hydroxyisocaproic acid productive strain, strain HICA432, which is used in Examples 1 to 48.

The strain HICA432 has been ascertained to be capable of producing from xylose not only the 2-hydroxyisocaproic acid, but also phenyllactic acid. Accordingly, in the following, the strain HICA432 is also called a 2-hydroxyisocaproic acid productive strain and a phenyllactic acid productive strain.

EXAMPLE 75

750 parts by weight of hemicellulose was introduced into 3,000 parts by weight of 1% hydrochloric acid, and these were stirred at 130° C. for 8 hours. After the reaction was completed, the reaction mixture was neutralized with a 10% sodium hydroxide solution. Thereafter, 1,800 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 550 parts by weight of xylose.

The xylose thus obtained was identified and ascertained as such by ion-exchange chromatography (TSKgel Sugar AXG Column, available from Tosoh Corporation).

550 parts by weight of this xylose was mixed with 27,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 270 parts by weight of a pre-culture fluid of phenyllactic acid productive strain HICA432 isolated in the manner as described previously was added thereto by means of a syringe when the bottle was kept hermetically stoppered, followed by a static culture at 30° C. for 6 days. Thereafter, the culture fluid was filtered, and the water and volatile components of the filtrate obtained were evaporated off under normal-temperature reduced pressure, followed by purification to obtain 10 parts by weight of phenyllactic acid.

The $^{13}$C-NMR (100 MHz, TMS, CDCl$_3$) of the phenyllactic acid thus obtained was measured to obtain the results (δ/ppm) of 177.92, 137.63, 130.30, 129.46, 127.82, 72.05, 40.38, and it was ascertained that the desired phenyllactic acid was obtained.

Its stereostructure was also evaluated using an optically active column (CYCLODEX-B, trade name; available from J & W Scientific Co.). As a result, it was ascertained that the phenyllactic acid obtained was in the L-form.

Using a reactor having a Dean-Stark trap, 10 parts by weight of the phenyllactic acid and 0.018 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 44 hours, and the aliphatic polyester obtained had a weight-average molecular weight of 200,000.

The aliphatic polyester thus obtained, having a weight-average molecular weight of 200,000, was dissolved in chloroform. From the solution obtained, a film was formed by casting. The formed film was colorless and had the following physical properties.
Thickness: 38 to 39 µm
Tensile strength: 70 MPa (yield), 69 MPa (breaking)
Elongation: 13%

EXAMPLE 76

Using phenyllactic acid obtained through the same procedure as in Example 75, a polyester was synthesized. Using the reactor having a Dean-Stark trap, 10 parts by weight of the phenyllactic acid and 0.02 part by weight of zinc chloride were put into it and 100 parts by weight of 1,3-dichlorobenzene was added thereto to effect azeotropic dehydration in an atmosphere of nitrogen, and the water having gathered in the Dean-Stark trap was appropriately removed. The polymerization time was 16 hours, and the aliphatic polyester obtained had a weight-average molecular weight of 50,000.

The aliphatic polyester thus obtained, having a weight-average molecular weight of 50,000, was dissolved in chloroform. From the solution obtained, a film was formed by casting. The formed film was colorless and had the following physical properties.
Thickness: 39 to 40 μm
Tensile strength: 23 MPa (yield), 20 MPa (breaking)
Elongation: 3%

EXAMPLE 77

Using phenyllactic acid obtained through the same procedure as in Example 75, it was converted into a cyclic dimer lactide in the following way.

Using the reactor having a Dean-Stark trap, 10 parts by weight of the phenyllactic acid and 0.20 part by weight of p-toluenesulfonic acid were put into it and 600 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The residue formed was recrystallized from ether to obtain 8.7 parts by weight of a cyclic dimer lactide.

8.7 parts by weight of the cyclic dimer lactide and 0.01 part by weight of tin chloride were heated at 160° C. for 10 hours in an atmosphere of nitrogen to effect ring-opening polymerization. The aromatic polyester thus obtained had a weight-average molecular weight of 190,000.

The aromatic polyester thus obtained, having a weight-average molecular weight of 190,000, was dissolved in chloroform. From the solution obtained, a film was formed by casting. The formed film was colorless and had the following physical properties.
Thickness: 39 to 40 μm
Tensile strength: 69 MPa (yield), 69 MPa (breaking)
Elongation: 12%

EXAMPLE 78

Using a cyclic dimer lactide obtained through the same procedure as in Example 77, an aromatic polyester was synthesized. That is, 8.7 parts by weight of the cyclic dimer lactide and 0.007 part by weight of tin octylate were heated at 180° C. for 33 hours in an atmosphere of nitrogen to effect ring-opening polymerization. The aromatic polyester thus obtained had a weight-average molecular weight of 700,000.

The aromatic polyester thus obtained, having a weight-average molecular weight of 700,000, was dissolved in chloroform. From the solution obtained, a film was formed by casting. The formed film was colorless and had the following physical properties.
Thickness: 39 to 40 μm
Tensile strength: 98 MPa (yield), 98 MPa (breaking)
Elongation: 25%

EXAMPLE 79

750 parts by weight of hemicellulose was introduced into 3,000 parts by weight of 1% hydrochloric acid, and these were stirred at 130° C. for 8 hours. After the reaction was completed, the reaction mixture was neutralized with a 10% sodium hydroxide solution. Thereafter, 1,800 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 550 parts by weight of xylose.

The xylose thus obtained was identified and ascertained as such by ion-exchange chromatography (TSKgel Sugar AXG Column, available from Tosoh Corporation).

550 parts by weight of this xylose was mixed with 27,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 270 parts by weight of a pre-culture fluid of 2-hydroxyisocaproic acid productive strain HICA432 isolated in the manner as described previously was added thereto by means of a syringe when the bottle was kept hermetically stoppered, followed by a static culture at 30° C. for 6 days. Thereafter, the culture fluid was filtered, and the water and volatile components of the filtrate obtained were evaporated off under normal-temperature reduced pressure, followed by purification to obtain 12 parts by weight of 2-hydroxyisocaproic acid.

The $^{13}$C-NMR (100 MHz, TMS, CDCl$_3$) of the 2-hydroxyisocaproic acid thus obtained was measured to obtain the results (δ/ppm) of 180.25, 68.95, 43.16, 24.45, 23.20, 21.42. Thus, it was ascertained that the desired 2-hydroxyisocaproic acid was obtained.

Its stereostructure was also evaluated using an optically active column (CYCLODEX-B, trade name; available from J & W Scientific Co.). As a result, it was ascertained that the phenyllactic acid obtained was in the L-form.

Using the reactor having a Dean-Stark trap, 12 parts by weight of the 2-hydroxyisocaproic acid and 0.018 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 44 hours, and the polyester obtained had a weight-average molecular weight of 220,000.

The polyester thus obtained, having a weight-average molecular weight of 220,000, was dissolved in chloroform. From the solution obtained, a film was formed by casting. The formed film was colorless and had the following physical properties.
Thickness: 38 to 39 μm
Tensile strength: 67 MPa (yield), 67 MPa (breaking)
Elongation: 16%

EXAMPLE 80

Using 2-hydroxyisocaproic acid obtained through the same procedure as in Example 79, a polyester was synthesized. Using the reactor having a Dean-Stark trap, 12 parts by weight of the 2-hydroxyisocaproic acid and 0.02 part by weight of zinc chloride were put into it and 100 parts by weight of 1,3-dichlorobenzene was added thereto to effect azeotropic dehydration in an atmosphere of nitrogen, and the water having gathered in the Dean-Stark trap was appropriately removed. The polymerization time was 16 hours, and the aliphatic polyester obtained had a weight-average molecular weight of 60,000.

The aliphatic polyester thus obtained, having a weight-average molecular weight of 60,000, was dissolved in chloroform. From the solution obtained, a film was formed by casting. The formed film was colorless and had the following physical properties.
Thickness: 39 to 40 μm
Tensile strength: 23 MPa (yield), 21 MPa (breaking)
Elongation: 3%

EXAMPLE 81

Using 2-hydroxyisocaproic acid obtained through the same procedure as in Example 79, it was converted into a cyclic dimer lactide in the following way.

Using the reactor having a Dean-Stark trap, 12 parts by weight of the 2-hydroxyisocaproic acid and 0.24 part by weight of p-toluenesulfonic acid were put into it and 600 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The residue formed was recrystallized from ether to obtain 9.8 parts by weight of a cyclic dimer lactide.

The $^{13}$C-NMR (100 MHz, TMS, CDCl$_3$) of the cyclic dimer lactide obtained was measured to obtain the results (δ/ppm) of 167.33, 74.14, 38.87, 23.89, 23.03, 21.33. Thus, it was ascertained that the desired cyclic dimer lactide was obtained.

9.8 parts by weight of the cyclic dimer lactide and 0.013 part by weight of tin chloride were heated at 150° C. for 12 hours in an atmosphere of nitrogen to effect ring-opening polymerization. The aliphatic polyester thus obtained had a weight-average molecular weight of 180,000.

The $^{13}$C-NMR (100 MHz, TMS, CDCl$_3$) of this aliphatic polyester was measured to obtain the results (δ/ppm) of 169.78, 71.38, 39.33, 24.53, 23.00, 21.43. Thus, it was ascertained that the desired aliphatic polyester was synthesized.

The aliphatic polyester thus obtained, having a weight-average molecular weight of 180,000, was dissolved in chloroform. From the solution obtained, a film was formed by casting. The formed film was colorless and had the following physical properties.
Thickness: 38 to 39 μm
Tensile strength: 68 MPa (yield), 68 MPa (breaking)
Elongation: 13%

EXAMPLE 82

Using a cyclic dimer lactide obtained through the same procedure as in Example 81, an aliphatic polyester was synthesized. That is, 7.4 parts by weight of the cyclic dimer lactide and 0.011 part by weight of tin octylate were heated at 180° C. for 30 hours in an atmosphere of nitrogen to effect ring-opening polymerization. The aliphatic polyester thus obtained had a weight-average molecular weight of 680,000. Its $^{13}$C-NMR was measured to find that the same spectrum as that in Example 81 was obtained, and it was ascertained that the desired aliphatic polyester was obtained.

The aliphatic polyester thus obtained, having a weight-average molecular weight of 680,000, was dissolved in chloroform. From the solution obtained, a film was formed by casting. The formed film was colorless and had the following physical properties.
Thickness: 38 to 39 μm
Tensile strength: 98 MPa (yield), 98 MPa (breaking)
Elongation: 30%

The following Examples 83 to 91 concern the polyester production process comprising the step of obtaining the substituted α-hydroxy acid by the fermentation of cellulose and xylose with a microorganism, which is described in the fourth embodiment.

As the microorganism, used is an isolated strain of *Clostridium beijerinckii* strain HICA432 (FERMP-18373), obtained upon studies of the ability to further produce the substituted α-hydroxy acid from cellulose and xylose with respect to the 2-hydroxyisocaproic acid productive strain, strain HICA432, which was used in Examples 1 to 48.

The strain HICA432 has been ascertained to be capable of producing from cellulose and xylose not only the 2-hydroxyisocaproic acid, but also lactic acid and phenyllactic acid. Accordingly, in the following, the strain HICA432 is also called a 2-hydroxyisocaproic acid productive strain, a lactic acid productive strain and a phenyllactic acid productive strain.

EXAMPLE 83

Newspapers were cut in a size of 10 mm square, and 500 parts by weight of the same was introduced into 2,500 parts by weight of 20% sulfuric acid, and these were stirred at 180° C. for 12 hours. After the reaction was completed, the reaction mixture was neutralized with a 20% sodium hydroxide solution. Thereafter, 300 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 25 parts by weight of xylose and 180 parts by weight of glucose.

The xylose and glucose thus obtained were identified and ascertained as such by ion-exchange chromatography (TSK-gel Sugar AXG Column, available from Tosoh Corporation).

25 parts by weight and 180 parts by weight of these xylose and glucose, respectively, were mixed with 10,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 100 parts by weight of a pre-culture fluid of phenyllactic acid productive strain HICA432 isolated in the manner as described previously was added thereto by means of a syringe when the bottle was kept hermetically stoppered, followed by a static culture at 30° C. for 6 days. Thereafter, the culture fluid was filtered, and the water and volatile components of the filtrate obtained were evaporated off under normal-temperature reduced pressure, followed by purification to obtain 9 parts by weight of phenyllactic acid.

The $^{13}$C-NMR (100 MHz, TMS, CDCl$_3$) of the phenyllactic acid thus obtained was measured to obtain the results (δ/ppm) of 177.92, 137.63, 130.30, 129.46, 127.82, 72.05, 40.38, and it was ascertained that the desired phenyllactic acid was obtained.

Its stereostructure was also evaluated using an optically active column (CYCLODEX-B, trade name; available from J & W Scientific Co.). As a result, it was ascertained that the phenyllactic acid obtained was in the L-form.

Using the reactor having a Dean-Stark trap, 9 parts by weight of the phenyllactic acid and 0.018 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 44 hours, and the aliphatic polyester obtained had a weight-average molecular weight of 120,000.

The aliphatic polyester thus obtained, having a weight-average molecular weight of 120,000, was dissolved in chloroform. From the solution obtained, a film was formed by casting. The formed film was colorless and had the following physical properties.
Thickness: 39 to 40 μm
Tensile strength: 50 MPa (yield), 49 MPa (breaking)
Elongation: 5%

EXAMPLE 84

Using phenyllactic acid obtained through the same procedure as in Example 83, a polyester was synthesized. Using the reactor having a Dean-Stark trap, 9 parts by weight of the phenyllactic acid and 0.015 part by weight of tin powder were put into it and 100 parts by weight of diphenyl ether was added thereto to effect azeotropic dehydration at 130° C./12 mmHg, and the water having gathered in the Dean-Stark trap was appropriately removed. The polymerization time was 48 hours, and the polyester obtained had a weight-average molecular weight of 220,000.

The aliphatic polyester thus obtained, having a weight-average molecular weight of 220,000, was dissolved in chloroform. From the solution obtained, a film was formed by casting. The formed film was colorless and had the following physical properties.
Thickness: 39 to 40 μm
Tensile strength: 74 MPa (yield), 73 MPa (breaking)
Elongation: 14%

EXAMPLE 85

Using phenyllactic acid obtained through the same procedure as in Example 83, it was converted into a cyclic dimer lactide in the following way.

Using the reactor having a Dean-Stark trap, 9 parts by weight of the phenyllactic acid and 0.18 part by weight of p-toluenesulfonic acid were put into it and 540 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The residue formed was recrystallized from ether to obtain 7.8 parts by weight of a cyclic dimer lactide.

7.8 parts by weight of the cyclic dimer lactide and 0.007 part by weight of tin octylate were heated at 180° C. for 33 hours in an atmosphere of nitrogen to effect ring-opening polymerization. The aromatic polyester thus obtained had a weight-average molecular weight of 700,000.

The aromatic polyester thus obtained, having a weight-average molecular weight of 700,000, was dissolved in chloroform. From the solution obtained, a film was formed by casting. The formed film was colorless and had the following physical properties.
Thickness: 39 to 40 μm
Tensile strength: 98 MPa (yield), 98 MPa (breaking)
Elongation: 25%

EXAMPLE 86

Newspapers were cut in a size of 10 mm square, and 500 parts by weight of the same was introduced into 2,500 parts by weight of 20% sulfuric acid, and these were stirred at 180° C. for 12 hours. After the reaction was completed, the reaction mixture was neutralized with a 20% sodium hydroxide solution. Thereafter, 300 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 25 parts by weight of xylose and 180 parts by weight of glucose.

The xylose and glucose thus obtained were identified and ascertained as such by ion-exchange chromatography (TSK-gel Sugar AXG Column, available from Tosoh Corporation).

25 parts by weight and 180 parts by weight of these xylose and glucose, respectively, were mixed with 10,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 100 parts by weight of a pre-culture fluid of phenyllactic acid/2-hydroxy-isocaproic acid productive strain HICA432 isolated in the manner as described previously was added thereto by means of a syringe when the bottle was kept hermetically stoppered, followed by a static culture at 30° C. for 6 days. Thereafter, the culture fluid was filtered, and the water and volatile components of the filtrate obtained were evaporated off under normal-temperature reduced pressure, followed by NMR analysis. As a result, it was ascertained that a mixture of 8.5 parts by weight of phenyllactic acid and 8.0 parts by weight of 2-hydroxyisocaproic acid was obtained.

Its $^1$H-NMR (400 MHz, TMS, DMSO-d$_6$) was measured to obtain the results (δ/ppm) as follows:
2-hydroxyisocaproic acid: 0.88 (t, 6H), 1.37 to 1.48 (m, 2H), 1.72 to 1.82 (m, 1H), 3.94 (dd, 1H);
phenyllactic acid: 2.82, 2.95, 4.16, 7.25.

The stereostructure of the 2-hydroxyisocaproic acid was also evaluated using an optically active column (CYCLO-DEX-B, trade name; available from J & W Scientific Co.).

As a result, it was ascertained that the 2-hydroxyisocaproic acid obtained was in the L-form.

Meanwhile, the stereostructure of the lactic acid was evaluated using an optically active column (RESTEK Column 13113, trade name; available from Uniflex Co.). As a result, it was ascertained that the phenyllactic acid obtained was in the L-form.

Using the reactor having a Dean-Stark trap, 8.0 parts by weight of the 2-hydroxyisocaproic acid, 8.5 parts by weight of the phenyllactic acid and 0.019 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 40 hours, and the polyester copolymer obtained had a weight-average molecular weight of 160,000.

The polyester copolymer thus obtained, having a weight-average molecular weight of 160,000, was dissolved in chloroform. From the solution obtained, a film was formed by casting. The formed film was colorless and had the following physical properties.
Thickness: 37 to 38 μm
Tensile strength: 60 MPa (yield), 60 MPa (breaking)
Elongation: 13%

EXAMPLE 87

Newspapers were cut in a size of 10 mm square, and 500 parts by weight of the same was introduced into 2,500 parts by weight of 20% sulfuric acid, and these were stirred at 180° C. for 12 hours. After the reaction was completed, the reaction mixture was neutralized with a 20% sodium hydroxide solution. Thereafter, 300 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 25 parts by weight of xylose and 180 parts by weight of glucose.

The xylose and glucose thus obtained were identified and ascertained as such by ion-exchange chromatography (TSK-gel Sugar AXG Column, available from Tosoh Corporation).

25 parts by weight and 180 parts by weight of these xylose and glucose, respectively, were mixed with 10,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 100 parts by weight of a pre-culture fluid of phenyllactic acid/lactic acid productive strain HICA432 isolated in the manner as described previously was added thereto by means of a syringe when the bottle was kept hermetically stoppered, followed by a static culture at 30° C. for 4 days. Thereafter, the culture fluid was filtered, and the water and volatile components of the filtrate obtained were evaporated off under normal-temperature reduced pressure, followed by NMR analysis. As a result, it was ascertained that a mixture of 4 parts by weight of phenyllactic acid and 5 parts by weight of lactic acid was obtained.

The results of analysis of the lactic acid are as follows:
$^1$H-NMR (400 MHz, TMS, DMSO-$d_6$) δ/ppm: 1.25 (d, J=6.8 Hz, 3H), 4.07 (q, J=6.8 Hz, 1H).

The results of analysis of the phenyllactic acid are also as follows:
$^1$H-NMR (400 MHz, TMS, DMSO-$d_6$) δ/ppm: 2.82, 2.95, 4.16, 7.25.

The stereostructure of the lactic acid was also evaluated using an optically active column (RESTEK Column 13113, trade name; available from Uniflex Co.). As a result, it was ascertained that the lactic acid obtained was in the DL-form.

Meanwhile, the stereostructure of the phenyllactic acid was evaluated using an optically active column (RESTEK Column 13113, trade name; available from Uniflex Co.). As a result, it was ascertained that the phenyllactic acid obtained was in the L-form.

Using the reactor having a Dean-Stark trap, 5 parts by weight of the lactic acid, 4 parts by weight of the phenyllactic acid and 0.018 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 40 hours, and the polyester copolymer obtained had a weight-average molecular weight of 130,000.

The polyester copolymer thus obtained, having a weight-average molecular weight of 130,000, was dissolved in chloroform. From the solution obtained, a film was formed by casting. The formed film was colorless and had the following physical properties.
Thickness: 38 to 39 μm
Tensile strength: 61 MPa (yield), 60 MPa (breaking)
Elongation: 6%

EXAMPLE 88

Newspapers were cut in a size of 10 mm square, and 500 parts by weight of the same was introduced into 2,500 parts by weight of 20% sulfuric acid, and these were stirred at 180° C. for 12 hours. After the reaction was completed, the reaction mixture was neutralized with a 20% sodium hydroxide solution. Thereafter, 300 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 22 parts by weight of xylose and 170 parts by weight of glucose.

The xylose and glucose thus obtained were identified and ascertained as such by ion-exchange chromatography (TSK-gel Sugar AXG Column, available from Tosoh Corporation).

22 parts by weight and 170 parts by weight of these xylose and glucose, respectively, were mixed with 10,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 100 parts by weight of a pre-culture fluid of 2-hydroxyisocaproic acid productive strain HICA432 isolated in the manner as described previously was added thereto by means of a syringe when the bottle was kept hermetically stoppered, followed by a static culture at 30° C. for 6 days. Thereafter, the culture fluid was filtered, and the water and volatile components of the filtrate obtained were evaporated off under normal-temperature reduced pressure, followed by purification to obtain 8 parts by weight of 2-hydroxyisocaproic.

The $^{13}$C-NMR (100 MHz, TMS, CDCl$_3$) of the 2-hydroxyisocaproic acid thus obtained was measured to obtain the results ($\delta$/ppm) of 180.25, 68.95, 43.16, 24.45, 23.20, 21.42. Thus, it was ascertained that the desired 2-hydroxyisocaproic acid was obtained.

Its stereostructure was also evaluated using an optically active column (CYCLODEX-B, trade name; available from J & W Scientific Co.). As a result, it was ascertained that the 2-hydroxyisocaproic acid obtained was in the L-form.

Using the reactor having a Dean-Stark trap, 8 parts by weight of the 2-hydroxyisocaproic acid and 0.018 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 44 hours, and the polyester obtained had a weight-average molecular weight of 100,000.

The polyester thus obtained, having a weight-average molecular weight of 100,000, was dissolved in chloroform. From the solution obtained, a film was formed by casting. The formed film was colorless and had the following physical properties.
Thickness: 39 to 40 μm
Tensile strength: 51 MPa (yield), 50 MPa (breaking)
Elongation: 6%

EXAMPLE 89

Using 2-hydroxyisocaproic acid obtained through the same procedure as in Example 88, a polyester was synthesized. Using the reactor having a Dean-Stark trap, 8 parts by weight of the 2-hydroxyisocaproic acid and 0.015 part by weight of tin powder were put into it and 100 parts by weight of diphenyl ether was added thereto to effect azeotropic dehydration at 130° C./12 mmHg, and the water having gathered in the Dean-Stark trap was appropriately removed. The polymerization time was 48 hours, and the polyester obtained had a weight-average molecular weight of 200,000.

The aliphatic polyester thus obtained, having a weight-average molecular weight of 200,000, was dissolved in chloroform. From the solution obtained, a film was formed by casting. The formed film was colorless and had the following physical properties.
Thickness: 39 to 40 μm
Tensile strength: 62 MPa (yield), 59 MPa (breaking)
Elongation: 18%

EXAMPLE 90

Using 2-hydroxyisocaproic acid obtained through the same procedure as in Example 88, it was converted into a cyclic dimer lactide in the following way.

Using the reactor having a Dean-Stark trap, 8 parts by weight of the 2-hydroxyisocaproic acid and 0.16 part by weight of p-toluenesulfonic acid were put into it and 400 parts by weight of toluene was added thereto to effect azeotropic dehydration for 30 hours in an atmosphere of nitrogen, and the water having gathered in the Dean-Stark trap was appropriately removed. After the reaction was completed, the reaction mixture was washed with sodium hydrogencarbonate, and the toluene was evaporated off. The residue formed was recrystallized from ether to obtain 6.5 parts by weight of a cyclic dimer lactide.

The $^3$C-NMR (100 MHz, TMS, CDCl$_3$) of the cyclic dimer lactide obtained was measured to obtain the results ($\delta$/ppm) of 167.33, 74.14, 38.87, 23.89, 23.03, 21.33. Thus, it was ascertained that the desired cyclic dimer lactide was obtained.

6.5 parts by weight of the cyclic dimer lactide and 0.010 part by weight of tin octylate were heated at 180° C. for 30 hours in an atmosphere of nitrogen to effect ring-opening polymerization. The aliphatic polyester thus obtained had a weight-average molecular weight of 680,000.

The $^{13}$C-NMR (100 MHz, TMS, CDCl$_3$) of this aliphatic polyester was measured to obtain the results ($\delta$/ppm) of 169.78, 71.38, 39.33, 24.53, 23.00, 21.43. Thus, it was ascertained that the desired aliphatic polyester was synthesized.

The aliphatic polyester thus obtained, having a weight-average molecular weight of 680,000, was dissolved in chloroform. From the solution obtained, a film was formed by casting. The formed film was colorless and had the following physical properties.
Thickness: 38 to 39 μm
Tensile strength: 98 MPa (yield), 98 MPa (breaking)
Elongation: 30%

EXAMPLE 91

Newspapers were cut in a size of 10 mm square, and 500 parts by weight of the same was introduced into 2,500 parts by weight of 20% sulfuric acid, and these were stirred at 180° C. for 12 hours. After the reaction was completed, the reaction mixture was neutralized with a 20% sodium hydroxide solution. Thereafter, 300 parts by weight of methanol was added to the reaction mixture, and thereafter the water-soluble residue formed was filtered off therefrom. The reaction mixture was further passed through an ion-exchange column (AMBERLITE IR-120B, trade name; available from Orugano K.K.), and the solvent was evaporated off. The resultant reaction mixture was separated and purified to obtain 25 parts by weight of xylose and 180 parts by weight of glucose.

The xylose and glucose thus obtained were identified and ascertained as such by ion-exchange chromatography (TSK-gel Sugar AXG Column, available from Tosoh Corporation).

25 parts by weight and 180 parts by weight of these xylose and glucose, respectively, were mixed with 10,000 parts by weight of a culture medium (10 g/l of peptone, 5 g/l of yeast extract, 2 g/l of meat extract, 5 g/l of NaCl, 2 g/l of cysteine hydrochloride and 5 g/l of calcium carbonate), and the mixture formed was injected into a pressure bottle. After the gaseous-phase portion in the bottle was displaced with nitrogen gas, the bottle was hermetically closed with a butyl rubber stopper, which was then treated in an autoclave (121° C., 98 kPa pressure, 10 minutes). Thereafter, the culture medium treated was cooled to 30° C., and 100 parts by weight of a pre-culture fluid of 2-hydroxyisocaproic acid/lactic acid productive strain HICA432 isolated in the manner as described previously was added thereto by means of a syringe when the bottle was kept hermetically stoppered, followed by a static culture at 30° C. for 3 days. Thereafter, the culture fluid was filtered, and the water and volatile components of the filtrate obtained were evaporated off under normal-temperature reduced pressure, followed by NMR analysis. As a result, it was ascertained that a mixture of 7 parts by weight of 2-hydroxyisocapric acid and 6 parts by weight of lactic acid was obtained.

Its $^1$H-NMR (400 MHz, TMS, DMSO-$d_6$) was measured to obtain the results (δ/ppm) as follows:

2-hydroxyisocaproic acid: 0.88 (t, 6H), 1.37 to 1.48 (m, 2H), 1.72 to 1.82 (m, 1H), 3.94 (dd, 1H);

lactic acid: 1.25 (d, J=6.8 Hz, 3H), 4.07 (q, J=6.8 Hz, 1H).

Its $^{13}$C-NMR (100 MHz, TMS, DMSO-$d_6$) was also measured to obtain the results (δ/ppm) as follows:

2-hydroxyisocaproic acid: 21.43, 23.12, 23.84, 42.84, 68.07, 176.23;

lactic acid: 20.39, 65.82, 176.42.

The stereostructure of the 2-hydroxyisocaproic acid was also evaluated using an optically active column (CYCLO-DEX-B, trade name; available from J & W Scientific Co.). As a result, it was ascertained that the 2-hydroxyisocaproic acid obtained was in the L-form.

Meanwhile, the stereostructure of the lactic acid was evaluated using an optically active column (RESTEK Column 13113, trade name; available from Uniflex Co.). As a result, it was ascertained that the lactic acid obtained was in the DL-form.

Using the reactor having a Dean-Stark trap, 7 parts by weight of the 2-hydroxyisocaproic acid, 6 parts by weight of the lactic acid and 0.018 part by weight of tin dichloride were put into it and 100 parts by weight of mesitylene was added thereto to effect azeotropic dehydration in an atmosphere of nitrogen, and the water having gathered in the Dean-Stark trap was appropriately removed. The polymerization time was 40 hours, and the aliphatic polyester copolymer obtained had a weight-average molecular weight of 170,000.

Its $^{13}$C-NMR (100 MHz, TMS, CDCl$_3$) was measured to obtain the results (δ/ppm) of 16.66, 21.43, 22.99, 24.55, 39.30, 68.97, 71.37, 169.51, 169.76. Thus, it was ascertained that the desired aliphatic polyester copolymer was synthesized.

The aliphatic polyester copolymer thus obtained, having a weight-average molecular weight of 170,000, was dissolved in chloroform. From the solution obtained, a film was formed by casting. The formed film was colorless and had the following physical properties.

Thickness: 38 to 39 μm
Tensile strength: 61 MPa (yield), 59 MPa (breaking)
Elongation: 14%

What is claimed is:

1. A process for producing a polyester comprising at least one repeating unit represented by the formula: —(O—CH(R)—C(O)—)—, the process comprising the steps of:
   (1) fermenting a saccharide with a microorganism, which is capable of forming a substituted α-hydroxy acid from the saccharide, to obtain at least one substituted α-hydroxy acid represented by the formula:

HO—CH(R)—C(O)OH, 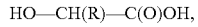

wherein R represents a hydrocarbon group having 1 to 10 carbon atoms;

(2) dehydrating the substituted α-hydroxy acid by two molecules to effect cyclic diesterification to obtain a cyclic dimer lactide; and
   (3) polymerizing the cyclic dimer lactide to produce the polyester,
   wherein the microorganism is an anaerobic bacterium belonging to a genus *Clostridium*.

2. The process according to claim 1, wherein the saccharide is glucose or xylose.

3. The process according to claim 2, which further comprises, prior to the steps (1) through (3), the step of subjecting a raw material containing cellulose or hemicellulose to hydrolysis to obtain the glucose or xylose.

4. The process according to claim 1, wherein the saccharide is starch.

5. The process according to claim 1, wherein the fermentation in the step (1) is carried out in the presence of pyruvic acid.

6. The process according to claim 1, wherein the bacterium of the genus *Clostridium* is *Clostridium beijerinckii* strain HICA432, FERMP-18373.

7. The process according to claim 1, wherein said polyester contains at least one repeating unit represented by the following Formulas (I) to (III):

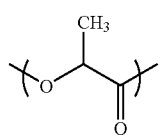

(I)

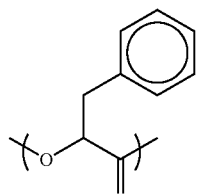

(II)

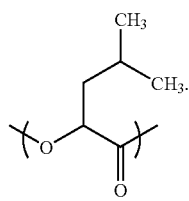

(III)

* * * * *

UNITED STATES PATENT AND TRADEMARK OFFICE
CERTIFICATE OF CORRECTION

PATENT NO.        : 7,273,734 B2
APPLICATION NO.   : 11/063776
DATED             : September 25, 2007
INVENTOR(S)       : Masato Minami et al.

It is certified that error appears in the above-identified patent and that said Letters Patent is hereby corrected as shown below:

COLUMN 2:

Line 25, "produces" should read --products--.

COLUMN 3:

Line 7, "lest" should read --least--.

COLUMN 4:

Line 6, "hydroxy" should read --α-hydroxy--.

COLUMN 9:

Line 47, "lest" should read --least--.

COLUMN 18:

Line 37, "detain" should read --detail--.

Signed and Sealed this

Twenty-seventh Day of May, 2008

JON W. DUDAS
*Director of the United States Patent and Trademark Office*